(12) United States Patent
Schroit et al.

(10) Patent No.: US 9,835,626 B2
(45) Date of Patent: Dec. 5, 2017

(54) METHODS AND COMPOSITIONS FOR ISOLATING EXOSOMES

(71) Applicants: Board of Regents, The University of Texas System, Austin, TX (US); Peregrine Pharmaceuticals, Inc., Tustin, CA (US)

(72) Inventors: Alan J. Schroit, Bellaire, TX (US); Philip E. Thorpe, Dallas, TX (US); Shelley P. M. Fussey, Houston, TX (US)

(73) Assignees: Board of Regents, The University of Texas System, Austin, TX (US); Peregrine Pharmaceuticals, Inc., Tustin, CA (US)

( * ) Notice: Subject to any disclaimer, the term of this patent is extended or adjusted under 35 U.S.C. 154(b) by 43 days.

(21) Appl. No.: 14/634,607

(22) Filed: Feb. 27, 2015

(65) Prior Publication Data

US 2015/0241431 A1 Aug. 27, 2015

Related U.S. Application Data

(60) Provisional application No. 61/945,718, filed on Feb. 27, 2014, provisional application No. 61/970,529, filed on Mar. 26, 2014.

(51) Int. Cl.
*G01N 33/53* (2006.01)
*G01N 33/574* (2006.01)
*G01N 33/50* (2006.01)

(52) U.S. Cl.
CPC ....... *G01N 33/574* (2013.01); *G01N 33/5076* (2013.01); *G01N 33/57484* (2013.01)

(58) Field of Classification Search
None
See application file for complete search history.

(56) References Cited

U.S. PATENT DOCUMENTS

| | | | |
|---|---|---|---|
| 8,901,284 B2 | 12/2014 | Vlassov et al. | |
| 9,005,888 B2 | 4/2015 | Antes et al. | |
| 2002/0102208 A1 | 8/2002 | Chinn et al. | |
| 2013/0273544 A1 | 10/2013 | Vlassov et al. | |
| 2013/0337440 A1 | 12/2013 | Antes | |

FOREIGN PATENT DOCUMENTS

| | | | |
|---|---|---|---|
| EP | 2 713 163 A1 | 4/2014 | |
| WO | WO 2007/036745 A2 | 4/2007 | |
| WO | WO 2012/087241 | * 6/2012 | |
| WO | WO 2012/087241 A1 | 6/2012 | |

OTHER PUBLICATIONS

Biancone et al (Nephrol Dial Transplant, 2012, 27:3037-3042).*
Keller et al (Cancer Letters, 2009, 278:73-81).*
Parolini et al (J Biological Chemistry, 2009, 284:34211-34222).*
Muller et al (J Bioanal Biomed, 2012, 4:46-60).*
Wu et al (Anal. Chem. 2013, 85:11265-11274).*
Moore, D. D. (2001. Commonly Used Reagents and Equipment. Current Protocols in Molecular Biology. 35:2:A.2.1-A.2.8).*
Brownlee et al., "A Novel "Salting-Out" Procedure for the Isolation of Tumor-Derived Exosomes", J. Immunol. Meth., 407:120-126, 2014.
Chen et al., "Phosphatidylserine Vesicles Enable Efficient En Bloc Transmission of Enteroviruses", Cell, 160:619-630, 2015.
György et al., "Membrane Vesicles, Current State-of-the-Art: Emerging Role of Extracellular Vesicles", Cell. Mol. Life Sci., 68:2667-2688, 2011.
Meckes et al., "Human tumor virus utilizes exosomes for intercellular communication", Proc. Natl. Acad. Sci. USA, 107(47):20370-20375, 2010.
Meckes and Raab-Traub, "Microvesicles and Viral Infection", J. Virology, 85 (24):12844-12854, 2011.
Mitchell et al., "Increased Exosome Production from Tumour Cell Cultures Using the Integra CELLine Culture System", J. Immunol. Meth., 335:98-105, 2008.
Muralidharan-Chari et al., "Microvesicles: Mediators of Extracellular Communication During Cancer Progression", J. Cell Sci. 123:1603-1611, 2010.
Parolini et al., "Microenvironmental pH is a Key Factor for Exosome Traffic in Tumor Cells", J. Biol. Chem., 284(49):34211-34222, 2009.
Schorey and Bhatnagar, "Exosome Function: From Tumor Immunology to Pathogen Biology", Traffic, 9:871-881, 2008.
Simons and Raposo, "Exosomes—Vesicular Carriers for Intercellular Communication", Curr. Opin. Cell Biol., 21:575-581, 2009.
Simpson & Mathivanan, "Extracellular Microvesicles: The Need for Internationally Recognised Nomenclature and Stringent Purification Criteria", J. Proteom Bioinf . . . , 5:2, 2012.
Sims et al., "Neural Stem Cell-Derived Exosomes Mediate Viral Entry", Intl. J. Nanomed., 9:4893-4897, 2014.
Szilagyi and Cunningham, "Identification and Characterization of a Novel Non-Infectious Herpes Simplex Virus-Related Particle", J. Gen. Virol., 72:661-668, 1991.
Taylor et al., "Exosome Isolation for Proteomic Analyses and RNA Profiling", Meth. Mol. Biol., 728:235-246, 2011.

(Continued)

*Primary Examiner* — Laura B Goddard
(74) *Attorney, Agent, or Firm* — Shelley P. M. Fussey

(57) ABSTRACT

Disclosed are surprising new methods and compositions for isolating extracellular microvesicles such as exosomes, particularly disease-related and phosphatidylserine (PS)-positive extracellular microvesicles as exemplified by tumor- and viral-derived exosomes. The methods of the invention are rapid, efficient, cost-effective and, importantly, are suitable for use with large volumes of biological fluids and produce antigenically intact extracellular microvesicles and exosomes. The methods and compositions are based on the surprising use of acetate buffers to isolate large quantities of extracellular microvesicles, particularly tumor-derived exosomes, from solution, without damaging their morphological or functional properties or antigenicity.

50 Claims, 18 Drawing Sheets
(9 of 18 Drawing Sheet(s) Filed in Color)

(56) References Cited

OTHER PUBLICATIONS

Thery et al., "Isolation and Characterization of Exosomes from Cell Culture Supernatants and Biological Fluids", Curr. Protoc. Cell Biol. 3.22.1-3.22.29, 2006.
Thery, "Exosomes: Secreted Vesicles and Intercellular Communications", F1000 Biol. Reports 3:15 (2011), doi: 10.3410/B3-15, 2011.
Zwaal and Deenen, "Interactions Between Proteins and Lipids from Human Red Cell Membranes", Chem. Phys. Lipids, 4:311-322, 1970.
Zwaal and Deenen, "Recombination in vitro of Proteins and Lipids from Mammalian Erythrocyte Membranes", Biochem. J., 122(5):62P-63P, 1971.
Cheruvanky et al., "Rapid Isolation of Urinary Exosomal Biomarkers Using a Nanomembrane Ultrafiltration Concentrator", Am. J. Physiol. Renal Physiol., 292:F1657-F1661, 2007.
Vlassov et al., "Exosomes: Current Knowledge of Their Composition, Biological Functions, and Diagnostic and Therapeutic Potentials", Biochim. Biophys. Acta,1820:940-948, 2012.
International Search Report for PCT/US15/18183, dated May 18, 2015.
GE Healthcare, "Ion Exchange Chromatography, Principles and Methods", a Handbook from GE Healthcare Life Sciences, first published Apr. 2004, © 2004-2016.
UC Davis ChemWiki, "Salting Out", Mar. 2014, last updated, Jul. 29, 2016.

\* cited by examiner

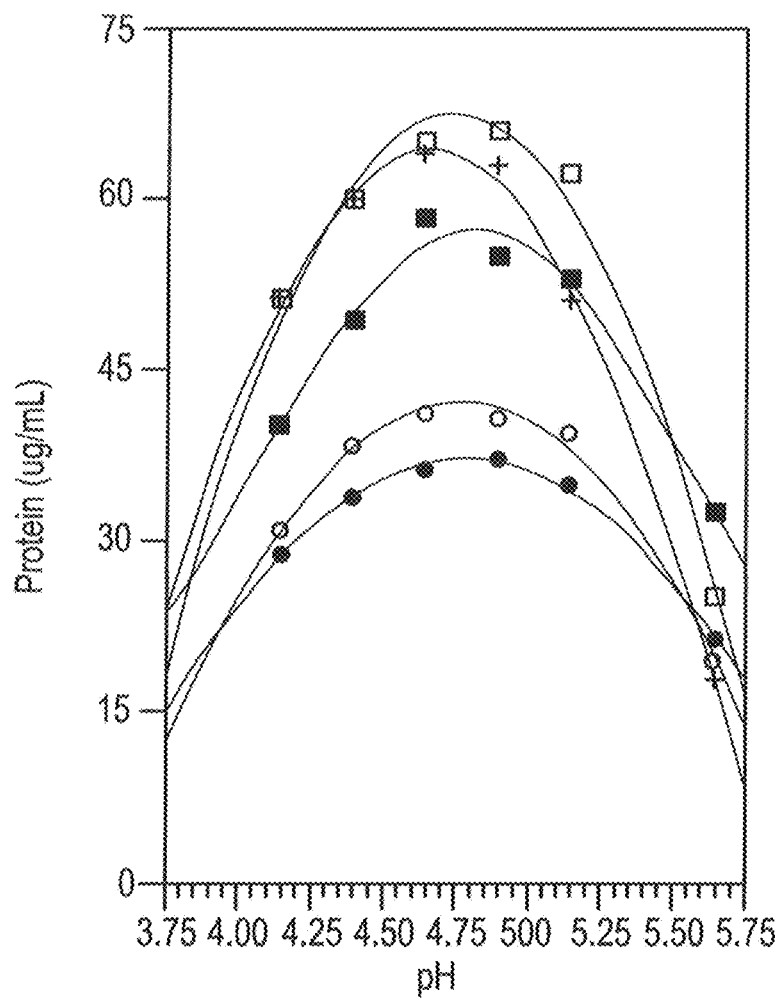

METHODS AND COMPOSITIONS FOR ISOLATING EXOSOMES

CROSS-REFERENCE TO RELATED APPLICATIONS

The present application claims priority to first U.S. provisional application Ser. No. 61/945,718, filed Feb. 27, 2014, and to second U.S. provisional application Ser. No. 61/970,529, filed Mar. 26, 2014, the entire disclosures of which applications, including the specification, claims and drawings are incorporated herein by reference without disclaimer.

BACKGROUND OF THE INVENTION

Field of the Invention

The present invention relates to the fields of biotechnology, and particularly to extracellular microvesicles such as exosomes. The invention provides surprising new methods and compositions for isolating disease-related and phosphatidylserine (PS)-positive extracellular microvesicles such as tumor- and viral-derived exosomes, particularly tumor-derived exosomes, which are especially suitable for use with large volumes of biological fluids and produce extracellular microvesicles and exosomes that are antigenically intact.

Description of the Related Art

Extracellular microvesicles are a class of membrane bound components released or secreted by cells, and include exosomes, ectosomes, microparticles or microvesicles and apoptotic bodies or blebs (György et al., 2011; Simpson & Mathivanan, 2012). Within this class of extracellular microvesicles, exosomes have gained particular attention in recent years.

Exosomes are typically described as 40-50 to 100 nanometer-sized membrane-derived vesicles and are known to be actively secreted by cells in vivo and in vitro. They are generated from the late endosomes by the inward budding and scission of the endosomal membrane, creating multivesicular bodies (MVBs) that contain intraluminal vesicles. These exosomes are released to the extracellular space upon fusion of the MVB with the plasma membrane. Because they originate from the cell's plasma membrane and are formed by invagination of the endosomal membrane, secreted exosomes possess plasma membrane and endosome proteins that encapsulate a cytosol-derived aqueous space.

Extracellular microvesicles such as exosomes exert a broad array of important physiological functions, e.g., by acting as molecular messengers that traffic information between different cell types. For example, exosomes deliver proteins, lipids and soluble factors including RNA and microRNAs (Thery et al., 2009) which, depending on their source, participate in signaling pathways that can influence apoptosis (Andreola et al., 2002; Huber et al., 2005; Kim et al., 2005), metastasis (Parolini et al., 2009), angiogenesis (Kim et al., 2005; Iero et al., 2008), tumor progression (Keller et al., 2009; Thery et al., 2002), thrombosis (Aharon & Brenner, 2009; Al Nedawi et al., 2005) and immunity by directing T cells towards immune activation (Andre et al., 2004; Chaput et al., 2005) or immune suppression (Szajnik et al., 2010; Valenti et al., 2007; Wieckowski et al., 2009).

Several techniques have been described for the isolation and purification of extracellular microvesicle and exosome populations from different sources, including from malignant effusions and the peripheral blood of cancer patients and from supernatants of in vitro cultivated cell lines and tumor cells. These methods include differential centrifugation, including an ultracentrifugation step (Thery et al., 2006); affinity chromatography (Taylor & Gercel-Taylor, 2008); polymer-mediated precipitation (Taylor et al., 2011), particularly using polyethylene glycol (PEG) of different molecular weights, including the Total Exosome Isolation Reagents from Life Technologies Corporation (U.S. Pat. No. 8,901,284) and ExoQuick™ (US 2013/0337440 A1); and capture on defined pore-size membranes (Grant et al., 2011), such as ExoMir™, which typically uses two filters of different pore-sizes connected in series (US 2013/0052647 A1).

However, the available techniques are limited by drawbacks in two important respects. Firstly, as applied to extracellular microvesicle and exosome preparation in general, they are time-consuming, cumbersome and/or costly, and limited by the amounts of material that can be processed. In particular, the techniques currently available for isolating extracellular microvesicles and exosomes all require a significant reduction in volume to obtain sufficient concentrations for study or use. The typical approach of concentrating the biological medium using ultracentrifugation before proceeding with exosome isolation is very time consuming and requires specialized laboratory equipment.

Secondly, the current techniques are particularly limited as they apply to tumor-derived extracellular microvesicle and exosomes. For example, the extra-corporeal removal of exosomes from the circulation of cancer patients has been proposed, in which patient's blood is pumped through a lectin-affinity column and then returned to the patient (U.S. Pat. No. 8,288,172). It has also been reported that tumor-derived exosomes can be purified using paramagnetic beads coated with antibodies against tumor-specific proteins such as HER2/neu (Koga et al., 2005). Kits using magnetic beads to capture specific exosomes are also available, such as Exo-Flow™ kits. In addition to the general drawbacks described above, such methods and kits are very limiting, requiring both advance knowledge of a particular exosome surface marker to be exploited in the antibody binding, as well as many detailed technical steps in the protocol, such as the preparation and use of biotinylated capture antibodies.

Therefore, there remains in the art a need for new and improved methods of isolating extracellular microvesicles such as exosomes, particularly disease-related and tumor-derived exosomes. The identification of simple and cost-effective new methods of isolating morphologically and antigenically intact extracellular microvesicles and exosomes would be an important advance. What is really needed is a method that is equipped to handle large volumes of biological materials, without specialized laboratory equipment and without the need for an early ultracentrifugation step, and particularly one that can be used to preferentially isolate disease-related and tumor-derived exosomes.

SUMMARY OF THE INVENTION

The present invention addresses the foregoing and other needs of the prior art by providing new methods and compositions for isolating extracellular microvesicles such as exosomes, particularly disease-related and phosphatidylserine (PS)-positive exosomes, including tumor-derived exosomes, which methods are rapid, efficient, cost-effective and suitable for use with large volumes of biological fluids. These methods are based on the surprising use of acetate buffers to isolate extracellular microvesicles such as exosomes from solution. The invention provides the ability to isolate large quantities of extracellular microvesicles and exosomes, particularly antigenically intact, disease-related and PS-positive exosomes such as tumor-derived exosomes, which are indistinguishable from those prepared by the current ultracentrifugation methods, the latter of which are time-consuming, cumbersome and volume-limited.

The invention is particularly suitable for purifying or isolating disease-related, viral- and tumor-derived exosomes, which express the negatively-charged phospholipid phosphatidylserine (PS), on their surface, typically in association with non-lipid membrane components, such as membrane proteins. The acetate buffers surprisingly neutralize the surface charge of the extracellular microvesicles and exosomes, thus removing them from solution, without damaging the morphological or functional properties of the resulting extracellular microvesicles and exosomes, and particularly whilst maintaining their original antigenic profile, such that they are "antigenically intact". Such disease-related exosomes include those from cells infected with a virus or intracellular parasite or pathogen, which cause the host cell to externalize PS, and are preferably tumor-derived exosomes, which typically contain a significant amount of PS on their surface.

A broadly applicable embodiment of the invention is a method of isolating disease-related extracellular microvesicles from a biological fluid, wherein the disease-related extracellular microvesicles have negatively-charged phosphatidylserine on their surface; such a method comprising contacting a sample of the biological fluid with an acetate buffer at a pH and concentration effective to precipitate disease-related extracellular microvesicles from the biological fluid and collecting disease-related extracellular microvesicles from the precipitate, thereby isolating the disease-related extracellular microvesicles.

Such methods include those for isolating extracellular microvesicles from a virally-infected cell, comprising contacting a biological fluid that contains the viral-derived extracellular microvesicles with an acetate buffer at a pH and concentration effective to precipitate the viral-derived extracellular microvesicles from the biological fluid and collecting the viral-derived extracellular microvesicles from the precipitate, thereby isolating the viral-derived extracellular microvesicles. The viral methods preferably isolate the extracellular viral-derived microvesicles substantially free from infectious virus.

The methods of the invention further include those for isolating tumor-derived extracellular microvesicles from a biological fluid, comprising contacting a sample of the biological fluid with an acetate buffer at a pH and concentration effective to precipitate tumor-derived extracellular microvesicles from the biological fluid and collecting tumor-derived extracellular microvesicles from the precipitate, thereby isolating the tumor-derived extracellular microvesicles.

Other examples of disease-related extracellular microvesicles are those derived from a cell infected with an intracellular parasite or pathogen.

In the foregoing methods, the disease-related, viral-derived and tumor-derived extracellular microvesicles are preferably disease-related, viral-derived and tumor-derived exosomes. Preferably, the disease-related, viral-derived and tumor-derived extracellular microvesicles and exosomes are isolated without substantially damaging their morphological or functional properties or cell surface antigens. Human extracellular microvesicles, such as human tumor exosomes can be isolated by the invention.

By applying the invention to all disease-related extracellular microvesicles, such as disease-related exosomes, phosphatidylserine will preferably be present on the surface of the extracellular microvesicles, more preferably in association with non-lipid membrane components, wherein the non-lipid membrane components comprise membrane proteins. In this regard, the acetate buffer is believed to neutralize the surface charge of the phosphatidylserine on the disease-related extracellular microvesicles, thereby precipitating the disease-related extracellular microvesicles from the biological fluid.

Accordingly, the invention particularly provides methods for use with biological fluids that contain a mixed population of extracellular microvesicles comprising disease-related and normal extracellular microvesicles, wherein the methods selectively precipitate the disease-related extracellular microvesicles from the mixed population, as opposed to the normal extracellular microvesicles. Embodiments of this are methods for use with biological fluids that contain a mixed population of exosomes comprising tumor-derived and normal exosomes, wherein the methods selectively precipitate the tumor-derived exosomes from the mixed population, as opposed to the normal exosomes.

Such methods can comprise:
(a) obtaining a biological fluid containing a mixed population of exosomes that includes tumor-derived exosomes and non-tumor exosomes;
(b) contacting the biological fluid with an acetate buffer at a pH and concentration effective to selectively precipitate tumor-derived exosomes, but not non-tumor exosomes, from the biological fluid;
(c) collecting the precipitate from step (b); wherein the precipitate selectively contains the tumor-derived exosomes; and
(d) re-suspending the precipitate in a substantially acetate-free buffer at about neutral pH, thereby providing a purified population of tumor-derived exosomes essentially free from non-tumor exosomes.

In more detail, these embodiments may comprise:
(a) obtaining a biological fluid containing a mixed population of exosomes that includes tumor-derived exosomes and non-tumor exosomes;
(b) performing a first low-speed centrifugation on the biological fluid to provide a clarified fluid essentially free from cells, cell debris and large membrane vesicles;
(c) incubating the clarified fluid with an acetate buffer at a pH and concentration effective, and for a time effective, to provide a turbid suspension comprising selectively precipitated tumor-derived exosomes, but substantially no precipitated non-tumor exosomes;
(d) subjecting the turbid suspension to a low-speed centrifugation to provide a precipitate and a supernatant; wherein the precipitate selectively comprises the tumor-derived exosomes;
(e) collecting the precipitate comprising the tumor-derived exosomes;
(f) re-suspending the precipitate in a substantially acetate-free buffer at about neutral pH, thereby providing a purified exosome population that comprises tumor-derived exosomes and is essentially free from non-tumor exosomes; and, optionally
(g) subjecting the purified exosome population to a further centrifugation to provide a pellet comprising non-exosome components and removing the pellet, thereby providing an essentially pure composition of tumor-derived exosomes that is substantially free from both non-tumor exosomes and non-exosome components.

As the invention effectively separates disease-related extracellular microvesicles from biological fluids that contain mixed populations of extracellular microvesicles, the invention further provides methods to obtain disease-related, preferably tumor-derived, extracellular microvesicles from the supernatant of diseased or tumor cells cultured in the presence of serum that contains normal extracellular microvesicles, preferably wherein the disease-related or tumor-derived extracellular microvesicles have negatively-charged phosphatidylserine on their surface. These methods comprise contacting the supernatant with an acetate buffer at a pH and concentration effective to selectively precipitate disease-related, preferably tumor-derived, extracellular microvesicles from the supernatant and collecting the precipitate, thereby obtaining disease-related, preferably tumor-derived, extracellular microvesicles from the supernatant without substantial contamination from normal extracellular microvesicles in the serum. A particular example is wherein mouse or human tumor cells are cultured in the presence of bovine or fetal bovine serum.

Another separating embodiment is a method to prepare serum that is substantially free from disease-related, preferably tumor-derived, extracellular microvesicles, wherein the disease-related or tumor-derived extracellular microvesicles have negatively-charged phosphatidylserine on their surface ("depleted serum"); the method comprising:
  (a) obtaining serum suspected of containing disease-related, preferably tumor-derived, extracellular microvesicles;
  (b) contacting the serum with an acetate buffer at a pH and concentration effective to precipitate disease-related, preferably tumor-derived, extracellular microvesicles from the serum; and
  (c) removing from the serum the precipitate formed in step (b), wherein the precipitate contains the disease-related, preferably tumor-derived, extracellular microvesicles, thereby providing a serum that is substantially free from disease-related, preferably tumor-derived, extracellular microvesicles.

These methods are applicable to virally-infected cells and include methods to prepare blood, serum or plasma that is substantially free from infectious virus and extracellular microvesicles derived from virally-infected cells (such as may be performed prior to a blood transfusion), comprising:
  (a) obtaining blood, serum or plasma suspected of containing infectious virus and extracellular microvesicles derived from virally-infected cells;
  (b) contacting the blood, serum or plasma with an acetate buffer at a pH and concentration effective to inactivate or precipitate the infectious virus and to precipitate the extracellular microvesicles from the blood, serum or plasma; and
  (c) removing from the blood, serum or plasma the precipitate formed in step (b), wherein the precipitate contains the inactivated or precipitated virus and the precipitated extracellular microvesicles, thereby providing blood, serum or plasma that is substantially free from infectious virus and extracellular microvesicles derived from virally-infected cells.

In further embodiments, the invention provides methods to detect disease-related, preferably tumor-derived, extracellular microvesicles in a clarified biological fluid, wherein the disease-related or tumor extracellular microvesicles have negatively-charged phosphatidylserine on their surface. These methods comprise contacting the clarified biological fluid with an acetate buffer at a pH and concentration effective to selectively precipitate disease-related, preferably tumor-derived, extracellular microvesicles from the clarified biological fluid and determining the presence of turbidity, as may be detected visually, in the resultant biological fluid; wherein the presence of turbidity in the resultant biological fluid indicates the detection of disease-related, preferably tumor-derived, extracellular microvesicles.

In other embodiments, the invention provides methods to diagnose an animal or patient having at least a first disease, such as cancer, characterized by the presence of disease-related extracellular microvesicles that have negatively-charged phosphatidylserine on their surface. These methods comprise detecting the presence of the disease-related, preferably tumor-derived, extracellular microvesicles in a biological fluid from the patient, thereby diagnosing the patient as having the first disease, such as cancer. Preferably, the disease-related or tumor-derived extracellular microvesicles are detected by a method comprising:
  (a) contacting the biological fluid with an acetate buffer at a pH and concentration effective to selectively precipitate the disease-related, preferably tumor-derived, extracellular microvesicles from the biological fluid; and
  (b) determining the presence of the precipitate in the resultant biological fluid; wherein the presence of the precipitate in the resultant biological fluid indicates the detection of the disease-related, preferably tumor-derived, extracellular microvesicles; and
  (c) optionally, wherein a first such disease is to be identified or differentiated from a second such disease, e.g., wherein cancer is to be identified or differentiated from a viral infection, the presence of the first disease is confirmed by testing for a further and/or independent biomarker or clinical sign of the first disease, such as a further and/or independent biomarker or clinical sign of cancer.

Further aspects of the invention are methods to monitor the disease burden of a patient having a first disease characterized by the amount of disease-related extracellular microvesicles that have negatively-charged phosphatidylserine on their surface, such as to monitor the tumor-burden of a cancer patient. These methods comprise measuring the amount of the disease-related, preferably tumor-derived, extracellular microvesicles in a biological fluid from the patient; wherein the amount of the disease-related, preferably tumor-derived, extracellular microvesicles is measured by a method comprising:
  (a) contacting the biological fluid with an acetate buffer at a pH and concentration effective to selectively precipitate the disease-related, preferably tumor-derived, extracellular microvesicles from the biological fluid; and
  (b) measuring the amount of the disease-related, preferably tumor-derived, extracellular microvesicles in the precipitate.

For example, methods to monitor the tumor-burden of a cancer patient comprise:
  (a) obtaining a series of biological fluid samples from the patient at a plurality of time points;
  (b) measuring the amount of tumor-derived extracellular microvesicles in the series of biological fluid samples by a method comprising:
    (i) contacting the series of biological fluid samples with an acetate buffer at a pH and concentration effective to selectively precipitate tumor-derived extracellular microvesicles from the series of biological fluid samples; and
    (ii) measuring the amount of tumor-derived extracellular microvesicles in the precipitates;

wherein an increase in the amount of tumor-derived extracellular microvesicles is indicative of an increased tumor-burden and a decrease in the amount of the tumor-derived extracellular microvesicles is indicative of a decreased tumor-burden.

In further embodiments, the invention provides an acetate buffer, and a composition of an acetate buffer, with a pH and concentration effective for use in diagnosis by precipitating disease-related, preferably tumor-derived, extracellular microvesicles that have negatively-charged phosphatidylserine on their surface from a biological fluid. The invention also provides an acetate buffer, and a composition of an acetate buffer, with a pH and concentration effective for use in therapy by precipitating disease-related, preferably tumor-derived, extracellular microvesicles that have negatively-charged phosphatidylserine on their surface from a biological fluid.

Other embodiments of the invention are kits for isolating disease-related, preferably tumor-derived, extracellular microvesicles from a biological fluid, wherein the disease-related extracellular microvesicles have negatively-charged phosphatidylserine on their surface. Such kits comprise an acetate buffer at a pH and concentration effective to precipitate the disease-related, preferably tumor-derived, extracellular microvesicles from a biological fluid; and preferably further comprise instructions for use. Such kits may also further comprise at least a first reagent for use in identifying or quantifying one or more biomarkers in a disease-related extracellular microvesicle, preferably an exosome; and/or for use in identifying or quantifying one or more further and/or independent biomarkers to identify particular diseases or to differentiate between diseases.

In all methods, compositions and kits of the invention, the acetate buffers are at a pH and concentration effective to selectively precipitate the disease-related, preferably tumor-derived, extracellular microvesicles, such as exosomes from biological fluids. These include acetate buffers having a pH of between about 4.25 and about 5.25; more preferably, having a pH of between about 4.5 and about 5.0; and most preferably, having a pH of about 4.75; and acetate buffers having a final concentration in the sample of biological fluid of between about 0.05M and about 0.25M; more preferably, of between about 0.05M and about 0.1M.

Acetate buffers comprising both sodium acetate and potassium acetate, and mixtures thereof, are effective. In certain embodiments, the acetate buffers are essentially free from volume excluding polymers, such as polyethylene glycol. An exemplary preferred embodiment is a sodium acetate buffer that has a pH of about 4.75 and a final concentration in the sample of about 0.1M.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The U.S. patent or application file contains at least one drawing executed in color. Copies of this U.S. patent or patent application publication with color drawing(s) will be provided by the Office upon request and payment of the necessary fee.

FIG. 1A, FIG. 1B and FIG. 1C. Salt and pH dependence of tumor exosome isolation. FIG. 1A and FIG. 1B, 4.5 mL aliquots of pre-cleared K1735 supernatants were mixed with $1/10^{th}$ volume (0.5 mL) of the 10× concentrated buffer solutions as indicated (●, 0.5M; ○, 0.367M; ■, 0.233M; □, 0.1M; +, 0.05M). The suspensions where incubated on ice for 60 min and centrifuged at 5,000 g for 10 min. The pellets were then solubilized and brought back to their initial volume and protein was assessed by Bradford assay. FIG. 1C, K1735 supernatant (right) or control media collected from the upper chamber of the CELLine flask (left) was mixed with $1/10^{th}$ volume of 1.0 M acetate pH 4.75 and photographed after 5 min incubation on ice.

FIG. 2A, 0.1 mL of 1M Na acetate was rapidly mixed with 0.9 mL of pre-cleared K1735 supernatants and incubated at the indicated temperature (■, 0° C.; ○, 20° C.; ●, 37° C.) while simultaneously monitoring turbidity. The arrow shows when the samples incubated at 0° C. and 37° C. were transferred to 37° C. and 0° C., respectively. FIG. 2B, Acetate/exosome mixtures were prepared as in FIG. 2A. Aliquots were diluted 2-fold for measurement of OD and the remaining suspension was centrifuged for 10 min at 5,000 g. Precipitated protein was quantified by Bradford assay.

FIG. 4A, precipitation is due to acetate, not the pH. Cleared tissue culture supernatants were mixed with $1/10^{th}$ volume of 1.0 M solutions of the indicated buffers (glycine HCl, citrate, acetate and control) for 1 hr at 4° C. The suspensions were then centrifuged at 5,000 g for 15 min. The supernatants were collected, centrifuged at 100,000 g for 1 hr and the concentration of protein in the pellets were determined by Bradford assay. FIG. 4B, precipitation is due to acetate, not the counter ion. Tissue culture supernatants (bottom, tubes 2 and 4) or media (top, tubes 1 and 3) from 4T1 breast carcinoma cells were separately mixed with $1/10^{th}$ volume of 10× sodium acetate (tubes 1 and 2) or 10× potassium acetate (tubes 3 and 4) at about pH 4.75 and left for 30 mins.

FIG. 7A, exosomes derived from normal mesothelial cells and from ovarian carcinoma cells obtained from the same patient were coupled to FITC-Annexin V latex beads and subjected to FACS analyses. Red line (left), normal mesothelial cell-derived exosomes; blue line (right), ovarian carcinoma-derived exosomes. FIG. 7B, exosomes derived from 4T1 breast carcinoma cells are PS-positive (blue line, right), as compared to BSA as a negative control (red line, left). FIG. 7C, exosomes derived from B16 melanoma cells are PS-positive (blue line, right), as compared to BSA as a negative control (red line, left).

FIG. 9A, characterization of the starting materials. Left panel, positive and negative controls: annexin 5 covalently coupled to aldehyde-activated latex beads (black (right) line) and BSA-blocked latex beads (red (left) line). Right panel, exosomes coupled to aldehyde-activated latex beads and labeled with FITC-annexin 5 in the presence of 1 mM $Ca^{2+}$: PS-positive exosomes from 4T1 breast carcinoma cells (black (right) line) and PS-negative exosomes from counterpart cells (red (left) line). FIG. 9B, FACS analysis of the exosome populations and mixture. Red fluorescence (N-Rho-PE) labeled, PS-negative exosomes and green fluorescence (N-NBD-PE) labeled, PS-positive exosomes were coupled to aldehyde-activated latex beads and analyzed by FACS. Top row, exosomes not subject to acetate precipitation (control); bottom row, solubilized acetate-precipitated exosomes (acetate). Left column, PS-negative exosome population (Rho PS−ve); middle column, PS-positive exosome population (NBD PS+ve); right column, mixture of equal amounts of PS-positive and PS-negative exosomes (Rho PS−ve NBD PS+ve).

FIG. 10A) or infected with SV40 (FIG. 10B) or HSV-1 (FIG. 10C) virus. Mock, SV40 or HSV-1 infections were harvested and subjected to acetate precipitation by mixing with $\frac{1}{10}^{th}$ volume of 1.0 M sodium acetate, pH 4.75. Depicted are centrifuge tubes after acetate precipitation, with clearly visible pellets from the SV40 (FIG. 10B) and HSV-1 (FIG. 10C) infections, as opposed to the mock infection (FIG. 10A).

FIG. 11A, FIG. 11B and FIG. 11C. FACS analyses of extracellular microvesicles and exosomes isolated from virally-infected cells. Separate populations of Vero cells were mock-infected (Vero, negative control) or infected with SV40 (SV40) or HSV-1 virus, harvested, subjected to acetate precipitation and any pellets resuspended. The resuspended pellet from the HSV-1 infection was subjected to Ficoll® gradient separation, yielding two fractions (HSV F5 and HSV F15). Samples from the mock (Vero), SV40 and HSV F5 and HSV F15 materials were bound to latex beads and analyzed by FACS to detect viral antigens specific for SV40 or HSV-1 (FIG. 11A); CD63, a marker of exosomes (FIG. 11B); and PS, as detected by Annexin V. Results are presented in comparison to the mock infection (Vero).

DETAILED DESCRIPTION OF EMBODIMENTS OF THE INVENTION

Figure 1C:
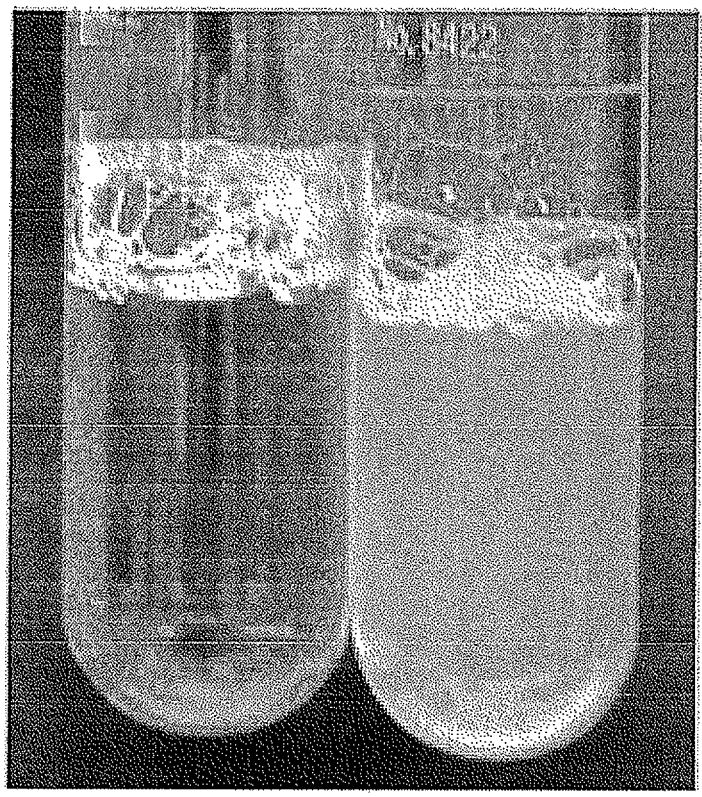

The last decade has seen an exponential growth in the number of studies and publications related to extracellular microvesicles such as exosomes. These studies range from methods for their isolation to the utility of certain extracellular microvesicles, particularly exosomes, in cancer diagnosis and their ability to mediate immune responses. Release of extracellular microvesicles occurs in both prokaryotes and eukaryotes and is important in a broad range of physiological and pathological processes.

A. Extracellular Microvesicles

Extracellular microvesicles are cell-derived and cell-secreted microvesicles which, as a class, include exosomes, exosome-like vesicles, ectosomes (which result from budding of vesicles directly from the plasma membrane), microparticles, microvesicles, shedding microvesicles (SMVs), nanoparticles and even (large) apoptotic blebs or bodies (resulting from cell death) or membrane particles, because such terms have been used interchangeably in the field (György et al., 2011; Simpson & Mathivanan, 2012).

"Extracellular microvesicles", as used herein, include extracellular microvesicles referred to by terminologies used for naming in the past, including terms based on the sample source from which the extracellular microvesicles were derived. As applied to tumor-derived exosomes in particular, the terms texosomes (tex) and oncosomes have been used and are included herein, as well as terms that reflect the particular type of cancer cell, such as prostate cancer cell-derived exosomes being termed prostasomes. In addition, exosomes isolated from dendritic cells have been termed dexosomes (dex), and other nomenclatures have been used, such as epididimosomes, argosomes, promininosomes, prostasomes and archeosomes (Simpson & Mathivanan, 2012).

Each of the foregoing entities, and mixtures and impure preparations thereof, are included within the term "extracellular microvesicles". Indeed, as the extracellular environment of cells and tissues will contain different types of extracellular microvesicles present simultaneously, mixtures of extracellular microvesicles are an important part of the present invention. Nonetheless, as various techniques and markers exist to identify particular types of extracellular microvesicles, as distinct from other types of extracellular microvesicles, the invention therefore encompasses substantially pure preparations of particular types of extracellular microvesicles.

Although the old terminologies are included herein, it is nonetheless preferable to define "extracellular microvesicles" using increasingly standardized nomenclature, refined by general consensus. Naming of extracellular microvesicles preferably considers three known mechanisms by which membrane vesicles are released into the extracellular microenvironment: exocytic fusion of multivesicular bodies, resulting in "exosomes"; budding of vesicles directly from the plasma membrane, resulting in "ectosomes"; and cell death, leading to "apoptotic blebs".

Recently, extracellular microvesicles have been described as having two major types: microvesicles or microparticles, which are together called "MVs" and "exosomes" themselves.

The microvesicles, microparticles or MVs are often described as activation- or apoptosis-induced microvesicles or microparticles. A third type of extracellular microvesicles is the apoptotic blebs, bodies and related entities.

The biogenesis of extracellular microvesicles essentially distinguishes "exosomes" from microvesicles/MVs and apoptotic bodies, as described in more detail below. See, also, Table 1 of György et al., 2011.

The term "microparticle", as used in the field of extracellular microvesicles, is also encompassed herein, but is less preferred as terminology, because "particle" suggests a solid, particulate structure, rather than a vesicular one. Therefore, the designation "microvesicle" is preferred in indicating membrane-limited structures. Nonetheless, endothelial cell- and platelet-derived microparticles have been described as "endothelial microparticles (EMPs)" and "platelet microparticles (PMPs)", which are included herein, as are all microvesicles, vesicular structures and membrane vesicles collectively falling within the term extracellular microvesicles.

As used herein, the terms "microvesicles" and "MVs" typically mean larger extracellular membrane vesicles or structures surrounded by a phospholipid bilayer that are about 100 nm to about 1,000 nm in diameter, or about 100 nm to about 400 nm in blood plasma. Microvesicles/MVs are formed by regulated release by budding or blebbing of the plasma membrane.

Within the class of extracellular microvesicles, important components are "exosomes" themselves, which are preferably described as between about 40 to 50 nm and about 100 nm in diameter and being membranous vesicles, i.e., vesicles surrounded by a phospholipid bilayer, of endocytic origin, which result from exocytic fusion, or "exocytosis" of multivesicular bodies (MVBs) (György et al., 2011; Simpson & Mathivanan, 2012). Less common, but included terms are also "vesiculation" and "trogocytosis".

As mentioned, the biogenesis of extracellular microvesicles essentially distinguishes "exosomes" from MVs and apoptotic bodies. Exosomes are actively secreted by cells in vivo and in vitro, both constitutively and upon induction, and are generated from the late endosomes, in particular, by the inward budding ("invagination") and scission of buds from the endosomal membrane into the lumen, creating MVBs that contain intraluminal vesicles. Exosomes are released to the extracellular space upon fusion of the MVB with the plasma membrane (see, for example, FIG. 2 of Simons & Raposo, 2009; and FIG. 1 of Schorey & Bhatnagar, 2008). Because exosomes originate from the cell's plasma membrane and are formed by invagination of the endosomal membrane, secreted exosomes possess plasma membrane and endosome or endosomal proteins that encapsulate a cytosol-derived aqueous space.

Exosomes incorporate a wide range of cytosolic and membrane components that reflect the properties of the parent cell. For example, the lumen of exosomes contain various components entrapped from the cell cytosol, including RNA and miRNA that express data signatures of disease that can be deciphered for the detection of neoplasia and identification of a specific tumor type (Taylor & Gercel-Taylor, 2008; Taylor et al., 2011; Rabinowits et al., 2009; Skog et al., 2008). Exosome membranes contain MHC class I and II (Iero et al., 2008), heat shock protein 70, Hsp 70 (Cho et al., 2009) that upregulates Th1-mediated immune responses and many cell surface components including, in the case of tumor-derived exosomes, tumor antigens from the plasma membrane of the parent cells. These observations suggest that tumor exosomes could be used as immunotherapeutics for the treatment of cancer. Indeed, recent clinical trials have indicated that "immunizations" with tumor exosomes have minimal side effects, are well tolerated, and elicit specific cytotoxic T cell responses (Escudier et al., 2005; Dai et al., 2008).

As exosome surface membranes reflect the plasma membrane of their parent cells, exosomes from diseased or aberrant cells are characterized by having phosphatidylserine (PS) on their surface, as opposed to exosomes from normal cells. The present invention can therefore be advantageously used in isolating disease-related exosomes that have PS exposed on their surface, preferably disease-related exosomes in which the PS exposed on their surface is present in association and/or approximation, or in operative association and/or close approximation, with non-lipid membrane components, preferably in association and/or approximation, or in operative association and/or close approximation, with membrane proteins. As described in detail below, such disease-related exosomes include those from cells infected with a virus or intracellular parasite, which cause the host cell to externalize PS, and are preferably tumor-derived exosomes, which typically contain a significant amount of PS on their surface.

"Exosome-like vesicles", which have a common origin with exosomes, are typically described as having size and sedimentation properties that distinguish them from exosomes and, particularly, as lacking lipid raft microdomains.

"Ectosomes", as used herein, are typically neutrophil- or monocyte-derived microvesicles.

"Membrane particles" (MPs), as used herein, are typically about 50-80 nm in diameter and originate from the plasma membrane. "Extracellular membraneous structures" also include linear or folded membrane fragments, e.g., from necrotic death, as well as membranous structures from other cellular sources, including secreted lysosomes and nanotubes.

As used herein, "apoptotic blebs or bodies" are typically about 1 to 5 µm in diameter and are released as blebs of cells undergoing apoptosis, i.e., diseased, unwanted and/or aberrant cells. They are characterized by PS externalization and may contain fragmented DNA.

B. Purification Techniques and Advantages of Acetate Precipitation

It is widely accepted in the literature that, in spite of extensive research, the rapidly emerging field of research into extracellular microvesicles remains technically difficult. For example, György et al., 2011 review major challenges and the problems and pitfalls associated with extracellular microvesicle preparation and measurement, including the difficulties associated with isolation of such materials.

The originally described and most widely used method for the purification of extracellular microvesicles such as exosomes involves escalating centrifugation steps that remove cells and cellular debris, followed by an ultracentrifugation step at 100,000 g for pelleting the extracellular microvesicles and exosomes (Thery et al., 2006). Other techniques include filtration through defined pore-sized membranes (Grant et al., 2011), polymer-based precipitation (Taylor et al., 2011), including PEG (e.g., U.S. Pat. No. 8,901,284 and US 2013/0337440 A1), and trapping on ELISA plates (Logozzi et al., 2009) or antibody-coated beads (Clayton et al., 2001). Highly specialized methods and kits are available to purify tumor-derived exosomes using magnetic beads coated with antibodies against tumor-specific proteins, such as HER2/neu (Koga et al., 2005), or other exosome surface markers (e.g., Exo-Flow™ kits).

Although most of those methods can, in principle, accommodate large volumes of material, they are limited in practice because they are laborious, very time consuming and require specialized laboratory equipment. As the vast majority of studies require the isolation of exosomes from large volumes of tissue culture supernatants, the significant reduction in volume that is required to obtain sufficient concentrations for study is a limitation in all the current techniques.

The present inventors therefore sought to investigate new methods for the purification or isolation of extracellular microvesicles such as exosomes, particularly disease-related and tumor-derived exosomes, from culture supernatants and biological fluids. They developed new and advantageous techniques based on the surprising use of acetate buffers (Example I and Example II). In contrast to the previous methods, this invention provides rapid and efficient isolation procedures yielding exosomes that are indistinguishable from those obtained by ultracentrifugation. Importantly, the new methods easily accommodate very large volumes of material and purification of extracellular microvesicles such as exosomes can be accomplished without specialized equipment and at minimal cost.

As extracellular microvesicles are present in both prokaryotes and eukaryotes and across all evolution (György et al., 2011), the invention may be used with any biological fluid from prokaryotes, eukaryotes, bacteria, fungi, yeast, invertebrates, vertebrates, reptiles, fish, insects, plants or animals, including mammals such as rodents and primates. For example, the biological fluid may be chicken serum, mouse serum, rat serum, rabbit serum, goat serum, lamb serum, sheep serum, horse serum, porcine serum, bovine serum (fetal bovine serum) and human serum. Preferred examples of biological fluids are murine, bovine or human biological fluids, as used to prepare extracellular microvesicles such as exosomes that are murine, bovine or human, respectively.

Examples of suitable biological fluids (or biofluids) are cell culture supernatants, whole blood, serum, plasma, ascites fluid, cerebral and cerebrospinal fluid, bone marrow aspirate, bronco-alveolar washing, urine, semen, vaginal fluid, mucous, saliva, sputum and clarified lysates from a biological tissue sample. Breast milk, tears, sweat, joint or synovial fluid, amniotic fluid, follicular fluid and faeces or faecal fluid may also be used. The biological fluid may be fresh or previously frozen and then thawed.

Preferred biological fluids for use with the invention are cell culture supernatants, serum, plasma and ascites fluid. For cell culture supernatants and conditioned media, the cells or population of cells, including sensitized cells, are cultured under conditions allowing release and/or secretion of extracellular microvesicles such as exosomes by the cells.

In certain embodiments, the biological fluid will be a "cleared" biological fluid such as a cleared cell culture supernatant, meaning that it has already been subjected to low-speed centrifugation. However, in other embodiments, the biological fluid can be subjected to low-speed centrifugation to remove cells, cell debris and large membrane vesicles as part of the invention, prior to contact with the acetate buffer.

The biological fluids may be obtained from diseased cells or tissues, as described in more detail below. For cancer, any malignant tumor may be used, including solid tumors and carcinomas, and exemplary tumors include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas and the like. From such examples, samples from melanoma, colorectal cancer, lung cancer, pancreatic cancer, liver cancer, prostate cancer, breast cancer and ovarian cancer are commonly used.

After the biological fluid sample is contacted with the acetate buffer to form the precipitate, which precipitate contains the extracellular microvesicles such as exosomes, the precipitate is collected, preferably by low-speed centrifugation. If desired, the isolated population of extracellular microvesicles such as exosomes can be further centrifuged to remove any contaminating components, thereby providing an essentially pure composition of extracellular microvesicles such as exosomes.

The isolated extracellular microvesicles such as exosomes are preferably washed to remove residual media and are further preferably "resolubilized" upon resuspension in acetate-free buffer at about neutral pH, physiological pH (such as about pH 7.35 to 7.45) and/or any standard laboratory pH, such as about pH 7.5 or 7.6 or so.

The methods of the invention are advantageously able to recover a substantial amount of extracellular microvesicles such as exosomes from biological fluids such as culture supernatants, for example, being able to recover at least about half of the extracellular microvesicles such as exosomes from a culture supernatant, up to and including recovering essentially all of the extracellular microvesicles such as exosomes from culture supernatants.

This simple and cost-effective method significantly increases the yield of extracellular microvesicles such as exosomes from an unlimited quantity of culture supernatants. Extracellular microvesicles such as exosomes isolated by this technique are also shown to be indistinguishable from those recovered by direct ultracentrifugation (Example III) and to be substantially antigenically intact (e.g., Example III and Example XIII). Given the common features of extracellular microvesicles such as exosomes, particularly tumor-derived exosomes, across species, the present invention can be used to isolate exosomes from cells and fluids from a wide range of sources, including from deposited tumor cell lines (e.g., Example IV), and from cells and fluids originating from murine and other rodents, bovine and human sources (as shown, for example, in Example V).

Although not believed to be necessary, the protocol of Example I and Example IV, particularly as used with the ATCC® deposited tumor cell lines in Example IV, may be used as a Reference Example for comparing to the present invention, including as a quantitative Reference Example.

The present use of acetate buffers to isolate extracellular microvesicles such as exosomes is believed to function by "charge neutralization" involving the negatively-charged phospholipid, phosphatidylserine (PS), which is present on the surface of extracellular microvesicles and exosomes, particularly on disease-related exosomes such as tumor-derived exosomes (Keller et al., 2009; Taylor et al., 2011; Grant et al., 2011). As shown by the present liposome studies (Example VIII), the same use of acetate does not precipitate lipid vesicles alone, even with PS on their surface. Therefore, it is believed that PS is required, but not sufficient, for vesicle isolation and that the present invention is effective for isolating disease-related extracellular microvesicles such as exosomes because they have PS on their surface in association with non-lipid membrane components, particularly membrane proteins.

The membrane surface of extracellular microvesicles, e.g., exosomes, reflects the plasma membrane of the cells from which they are derived. As PS is maintained on the inside of healthy or normal cells, extracellular microvesicles derived from normal cells are PS-negative. For example, Connor et al. (2010) reported that the majority of circulating platelet-derived extracellular microvesicles fail to bind annexin V, and so are PS-negative. In contrast, in various states of disease and/or cell activation, PS becomes exposed on the outside of the cell, so extracellular microvesicles such as exosomes derived from diseased, infected, unduly activated or otherwise aberrant cells are PS-positive, as described in more detail below.

It is not necessary to understand the precise mechanism responsible for acetate-based exosome precipitation and isolation in order to successfully practice the present invention. Nonetheless, the following observations and insights are provided. The mechanism does not appear to be due to precipitation at the isoelectric point, since extracellular microvesicles such as exosomes failed to precipitate when the solution was acidified with HCl or citrate. Interestingly, reviewing the literature over the last 40 years, the inventors noted that precipitation of vesicles formed by recombination of red cell apoproteins (Zwaal & van Deenen, 1970) was dependent on the presence of negatively-charged phosphatidic acid or PS. The inventors therefore believe that the principle mechanism responsible for the precipitation and isolation of extracellular microvesicles such as exosomes is acetate-mediated removal of the vesicle or exosome hydration layer that promotes hydrophobic interactions resulting in increasing aggregation and concomitant precipitation. The decrease in precipitation on either side of the preferred pH range (4.25 to 5.25, preferably 4.5 to 5.0, with an optimum of 4.75) is likely due to increased positive or negative surface charge that reinforces the hydration layer thereby necessitating decreasing salt to affect the same degree of precipitation.

In addition to the surprising use of acetate buffers in particular, the use of any buffer in the pH range of between about 4 and about 6 to effectively isolate extracellular microvesicles such as exosomes, particularly morphologically intact extracellular microvesicles and exosomes, runs contrary to information in the literature concerning the use of buffers in this pH range to completely lyse exosomes (lysis solution 1 and 2 in U.S. Pat. No. 8,530,228). Nonetheless, the present invention does provide for the preparation of morphologically intact extracellular microvesicles such as exosomes, indistinguishable from exosomes prepared by other techniques.

Comparison of the acidified versus ultracentrifuged extracellular microvesicle and exosome populations by flow cytometry, EM, SDS-PAGE and western blotting with alix and hsp70 antibodies indicated that both populations were indistinguishable from one another. Although there was an increase in α2-macroglobulin (the band at about 160 kDa) in the acetate-precipitated exosome population from K1735 melanoma cells, this is not a limitation of the invention. Firstly, extraneous protein precipitation is most likely dependent on the type of source cells, with α2-macroglobulin known to be produced by some melanoma and sarcoma cells (Morgan, 1984; Bizik et al., 1986). Indeed, α2-macroglobulin was not detectable in extracellular microvesicles and exosomes derived from B16 melanoma or TRAMP prostate carcinoma cells (Example IV). Secondly, although some extraneous protein precipitation will not interfere with nucleic acid-based exosome diagnostic assays, those extraneous proteins can anyway be easily removed, which would be preferred before immunotherapeutic use. In this case, once large volumes of culture supernatants are reduced to manageable volumes with acetate, 100,000 g centrifugation of the resolubilized precipitate can easily remove any contaminating proteins.

Preliminary studies have also shown that acetate buffers can be used to isolate extracellular microvesicles such as exosomes from whole human blood (Example VI). Using whole blood doped with known amounts of purified tumor-derived exosomes, acetate precipitation recovered about 40% and about 100% of the added exosomes from clotted serum samples and EGTA-plasma, respectively. There was a difference in the amount of protein recovered, which is believed to be due to precipitation of fibrinogen in the plasma samples. Any such fibrinogen can be easily removed, e.g., by pre-incubation at 56° C. for 3 min (Millar et al., 1971; Marx et al., 2008). Indeed, this step reduced the levels of extraneous protein in the acetate precipitated samples to levels comparable to those obtained for the serum samples, with essentially no loss of exosomes. As discussed above, the presence of some extraneous proteins in exosome preparations should not pose any problems for transcriptomic analysis. For use as immunogens or in other therapies, non-exosomal proteins can be easily removed by ultracentrifugation once volumes have been reduced to manageable volumes with acetate.

An important aspect of the present invention is the specificity for precipitating disease-related extracellular microvesicles such as exosomes, particularly viral- and tumor-derived extracellular microvesicles and exosomes, as opposed to extracellular microvesicles and exosomes from normal cells and fluids (Example VII and Example IX). This has significance for both practical laboratory studies and for diagnostic tests and kits.

The specificity of the invention leads to a number of embodiments where particular populations of extracellular microvesicles such as exosomes are prepared "substantially free" from other components. For example, disease-related extracellular microvesicles such as exosomes substantially free from non-disease-related extracellular microvesicles or exosomes, e.g., from normal cells; tumor-derived extracellular microvesicles such as exosomes substantially free from non-tumor-derived extracellular microvesicles or exosomes, e.g., from normal cells; viral-derived extracellular microvesicles such as exosomes substantially free from non-viral-derived extracellular microvesicles or exosomes, e.g., from normal cells; fluids such as serum substantially free from disease-related, tumor-derived and/or viral-derived extracellular microvesicles such as exosomes; fluids such as serum substantially free from infectious virus and from extracellular microvesicles such as exosomes derived from virally-infected cells; viral-derived extracellular microvesicles such as exosomes substantially free from infectious virus; disease-related, tumor-derived and/or viral-derived extracellular microvesicles such as exosomes substantially free from non-disease-related, non-tumor-derived and/or non-viral-derived extracellular microvesicles or exosomes and from non-exosome components or contaminants.

In all such contexts, compositions that are "substantially free" and "essentially free" from other recited component(s) are used to mean compositions that are sufficiently free from the other recited component(s) such that the other recited component(s) have essentially no material effect on the composition, up to and including no detectable effect, as measured, e.g., in a standard quantitative, or preferably functional assay for such other recited component(s). That is, the other recited component(s) do not materially, or even measurably, interfere with the function of the composition or otherwise cause any untoward reactions, properties or defects therein, as measured, e.g., in a standard quantitative, or preferably functional assay for the active components of the composition.

Similar meaning is ascribed to "substantially free" and "essentially free" in the terms substantially acetate-free buffer, essentially free from cells and essentially free from volume excluding polymers, such as polyethylene glycol.

For example, as the standard growth media for most cells in the laboratory include animal sera, such as bovine serum or fetal bovine serum, the serum in the media will typically contain a large amount of extracellular microvesicles, such as exosomes, from that animal source. Those media-derived extracellular microvesicles and exosomes can interfere with studies aimed at analyzing the extracellular microvesicles and exosomes secreted by the cultured cells. Options to address this problem are to include an extra step of depleting exosomes from the media/serum or to purchase and use exosome-depleted growth supplements, such as exosome-depleted fetal bovine serum (e.g., Exo-FBS™)

However, as the present invention provides the ability to isolate tumor-derived extracellular microvesicles such as exosomes separately from extracellular microvesicles and exosomes derived from normal cells (so-called "normal" extracellular microvesicles and "normal" exosomes), such laborious and/or costly procedures are no longer required when using the invention to isolate tumor-derived extracellular microvesicles such as tumor-derived exosomes directly from cultured tumor cells.

In addition, the ability to separate tumor-derived extracellular microvesicles such as tumor-derived exosomes from normal extracellular microvesicles and exosomes, as provided by the present invention, has importance for diagnostic tests and kits, including those to test fluids from human patients for the presence of tumor-derived extracellular microvesicles and exosomes. In this regard, a simple test to precipitate tumor-derived extracellular microvesicles such as tumor-derived exosomes could be added to the battery of tests performed on blood samples routinely obtained in doctor's visits. An initial positive in such a test would then be followed-up by further analysis of the precipitated tumor-derived extracellular microvesicles such as tumor-derived exosomes, particularly to test for biomarkers, such as RNA, micro RNA, DNA or protein biomarkers, along with further clinical assessment of the patient.

To further analyze the isolated extracellular microvesicles such as tumor-derived exosomes, a wide range of biomarkers are known, as described, e.g., in György et al., 2011, any one or more of which may be assessed as part of the present invention. By way of example, exosome biomarkers include Alix and hsp70, CD63 and caveolin-1 (Logozzi et al., 2009), CD81 and CD82. The biomarkers analyzed may be non-exosomal, such as tumor or viral markers. Biomarkers may be isolated by any means, such as electrophoretic separation, immunoisolation, chromatography or combinations thereof, and quantitated by any means, such as immunoassay, mass spectrometry or a combination thereof, including MALDI MS and immunoassays such as a Western blot, enzyme-linked immunoassay (ELISA), radioimmunoassay (RIA) or competitive binding assay.

As to further analysis of the isolated extracellular microvesicles such as tumor-derived exosomes, whether for scientific study and/or clinical diagnostic and prognostic purposes, it is a particular advantage of this invention that the isolated extracellular microvesicles such as exosomes are substantially "antigenically intact", such that they substantially retain their original surface markers and antigens in an "antibody-binding form". Moreover, the substantially antigenically intact extracellular microvesicles, such as exosomes, can be used in immunization to produce antibodies, including in immunizing experimental animals to obtain new therapeutic antibodies, such as humanized or human antibodies, which antibodies recognize the preserved antigens or markers, particularly tumor or viral antigens or markers, maintained on the extracellular microvesicles or exosomes.

As to the interior of the isolated extracellular microvesicles and exosomes, however, it is likely that the relatively low pH of the isolating methods also acidifies the interior of the vesicles. Accordingly, for analysis of nucleic acid biomarkers, e.g., by RT-PCR, it is preferable that the extracellular microvesicles and exosomes be restored towards neutral pH, physiological pH (such as about pH 7.35 to 7.45) or any standard laboratory pH (e.g., about pH 7.5 or 7.6) at least before analysis, and more preferably, in a timely manner after isolation and/or before any storage or freezing. Resuspending isolated extracellular microvesicles such as exosomes in an acetate-free buffer at a pH from about 7.0 to about pH 7.6 is anyway preferable, but is believed to be more important for nucleic acid analysis.

C. Acetate Buffers

As shown in Example I and FIG. 1A and FIG. 1B, the "salting-out" or precipitation method of isolating extracellular microvesicles such as exosomes, as provided by the invention, is effective across the entire range of acetate buffers. In particular, note that "acetate buffers", by their very nature, have a pH range of between about pH 3.7 and about pH 5.8, such as having a pH range of between about pH 3.75 and about pH 5.75, or as having a pH range of between about pH 3.7 and about pH 5.6.

For example, with reference to sodium acetate in particular, well-known resources such as the Buffer Reference Center of Sigma-Aldrich® show that sodium acetate-acetic acid buffer solutions have a useful pH range of between about pH 3.7 and about pH 5.6 (see also, Dawson, 1986). The Buffer Table below describes sodium acetate trihydrate, $CH_3COONa \cdot 3H_2O$, M. wt. 136.09, where a 0.2M-solution contains 27.22 g/l, and where x ml 0.2M-NaOAc and y ml 0.2M-HOAc are mixed.

| Buffer Table | | |
|---|---|---|
| pH, 18° C. | x ml 0.2M-NaOAc | y ml 0.2M-HOAc |
| 3.7 | 10.0 | 90.0 |
| 3.8 | 12.0 | 88.0 |
| 4.0 | 18.0 | 82.0 |
| 4.2 | 26.5 | 73.5 |
| 4.4 | 37.0 | 63.0 |
| 4.6 | 49.0 | 51.0 |
| 4.8 | 59.0 | 41.0 |
| 5.0 | 70.0 | 30.0 |
| 5.2 | 79.0 | 21.0 |
| 5.4 | 86.0 | 14.0 |
| 5.6 | 91.0 | 9.0 |

The invention is suitable for use with a range of acetate buffers, e.g., with monovalent or divalent cations, such as sodium acetate, potassium acetate (e.g., see Example II and FIG. 4B) and ammonium acetate, and mixtures thereof, with sodium acetate and potassium acetate being preferred, and sodium acetate being particularly preferred. Those other acetate buffers, such as potassium acetate and ammonium acetate, are also in the general pH of between about pH 3.7 and about pH 5.8, such as having a pH range of between about pH 3.75 and about pH 5.75, or as having a pH range of between about pH 3.7 and about pH 5.6.

As shown in Example I and FIG. 1A and FIG. 1B, the entire range of salt and pH conditions are effective in precipitating extracellular microvesicles such as tumor-derived exosomes, with meaningful levels of protein being recovered from all the test conditions. For example, by fitting the curves to the data points in FIG. 1A, it can be seen that acetate buffers from pH 3.75 to pH 5.75, and from 0.05M to 0.5M, are effective. The actual data points show that, across the full range of concentrations from 0.05M to 0.5M, effective precipitation occurred at pH 4.14, pH 4.39, pH 4.64, pH 4.89, pH 5.14 and pH 5.64 (FIG. 1A). Effective precipitation also occurred at each concentration tested, namely 0.05M, 0.1M, 0.233M, 0.367M and 0.5M (FIG. 1A). By fitting the curves to the data points, the pH optimum for each concentration can be determined as follows: pH 4.65 at 0.05M; pH 4.75 at 0.1M; pH 4.80 at 0.233M; pH 4.77 at 0.367M; and pH 4.78 at 0.5M (FIG. 1B).

However, despite acetate buffers across the entire ranges of pH and concentration being effective, certain preferred ranges can be selected. As shown in FIG. 1A, the present invention is effective using acetate buffers having a pH of between about pH 4.14 and about pH 5.25 or between about 4.25 and about 5.25, preferably having a pH of between about 4.5 and about 5.0, and at concentrations of between about 0.05M and about 0.25M, such as 0.05M, 0.1M and 0.233M, with concentrations of between about 0.05M and about 0.1M being preferred. For example, titration of tissue culture supernatants with 0.1M acetate to pH 4.75 is shown herein to result in immediate precipitation of virtually all the exosomes.

The invention therefore includes the use of acetate buffers having a pH of about 4.14, 4.25, 4.3, 4.39, 4.35, 4.4, 4.45, 4.5, 4.55, 4.6, 4.64, 4.65, 4.7, 4.75, 4.8, 4.85, 4.89, 4.9, 4.95, 5.0, 5.05, 5.1, 5.14, 5.15, 5.2, 5.25, 5.64 or about 5.75; more preferably, having a pH of about 4.5, 4.55, 4.6, 4.65, 4.7, 4.75, 4.8, 4.85, 4.9, 4.95 or 5.0; and most preferably, having a pH of about 4.65, 4.7, 4.75, 4.8 or 4.85.

The invention therefore includes the use of acetate buffers at a concentration of about 0.01M, 0.02M, 0.03M, 0.04M, 0.05M, 0.06M, 0.07M, 0.08M, 0.09M, 0.10M, 0.11M, 0.12M, 0.13M, 0.14M, 0.15M, 0.16M, 0.17M, 0.18M, 0.19M, 0.20M, 0.21M, 0.22M, 0.23M, 0.233M, 0.24M, 0.25M, 0.26M, 0.27M, 0.28M, 0.29M, 0.30M; 0.31M, 0.32M, 0.33M, 0.34M, 0.35M, 0.36M, 0.367M, 0.37M, 0.38M, 0.39M, 0.40M, 0.41M, 0.42M, 0.43M, 0.44M, 0.45M, 0.46M, 0.47M, 0.48M, 0.49M, 0.50M, 0.51M, 0.52M, 0.53M, 0.54M or 0.55M; and more preferably at a concentration of about 0.05M, 0.06M, 0.07M, 0.08M, 0.09M, 0.10M, 0.11M, 0.12M, 0.13M, 0.14M, 0.15M, 0.16M, 0.17M, 0.18M, 0.19M, 0.20M, 0.21M, 0.22M, 0.23M, 0.233M, 0.24M or 0.25M; and even more preferably, at a concentration of about 0.05M, 0.06M, 0.07M, 0.08M, 0.09M or 0.10M.

From space-filling (or 3D) models of the same data as in FIG. 1A, pH ranges of between about pH 4.14 and about pH 5.25, between about pH 4.14 and about pH 5.0, between about pH 4.39 and about pH 5.4, between about pH 4.39 and about pH 5.25 and between about pH 4.39 and about pH 5.14, and concentrations of between about 0.05M and 0.25M, between about 0.05M and 0.233M and between about 0.05M and 0.15M, are preferred; and pH ranges of between about pH 4.5 and about pH 5.4, between about pH 4.5 and about pH 5.25 and between about pH 4.5 and about pH 5.0, and concentrations of between about 0.05M and 0.233M, between about 0.05M and 0.15M and between about 0.05M and 0.1M are particularly preferred.

Even more preferred ranges are therefore between about pH 4.5 and about pH 5.25, or between about pH 4.5 and about pH 5.0, and concentrations of between about 0.05M and 0.15M, or between about 0.05M and 0.1M.

Any pH range or number can be combined with any concentration range or number. For example, within the preferred embodiments, the acetate buffer can have a pH of between about 4.25 and about 5.25 and a final concentration in the sample of between about 0.05M and about 0.25M; and more preferably, the acetate buffer has a pH of between about 4.5 and about 5.0 and a final concentration in the sample of between about 0.05M and about 0.1M. The currently most preferred embodiment is the use of sodium acetate buffer at a concentration of about 0.1M and a pH of about 4.75.

Throughout the discussion of "concentration", as used herein, the effective concentration is set forth as the "final concentration" in the sample of the biological fluid, such that, typically, 1/10th volume of 10× concentrated acetate buffer is added to the sample of the biological fluid. For example, 1/10th volume of 1.0M acetate buffer is added to give a final concentration in the sample of 0.1M.

In certain embodiments, the acetate buffers for use in the invention will preferably be essentially free from volume excluding polymers, such polyethylene glycol (PEG); dextrans such as dextran sulfate and dextran acetate; and hydrophilic polymers such as polyvinyl alcohol, polyvinyl acetate or polyvinyl sulfate.

D. Phosphatidylserine Exposure in Diseases

Isolation of extracellular microvesicles such as exosomes from tumors is an important aspect of the invention. In addition to tumor-derived extracellular microvesicles and exosomes, as those compositions reflect that of the originating cell, other sources of PS-positive extracellular microvesicles and exosomes that can be isolated using the invention are those from cells infected with a wide range of pathogens.

For example, intracellular parasites, such as the parasitic protozoan, *Leishmania amazonensis* (Zandbergen et al., 2006; Wanderley et al., 2009; Wanderley et al., 2013), *Plasmodium falciparum*, which causes malaria (Eda & Sherman, 2002; Pattanapanyasat et al., 2010; U.S. Pat. No. 7,262,167) and *Trypanosoma cruzi*, a parasitic protozoan (DaMatta et al., 2007), all cause PS exposure. Likewise, *Schistosoma*, parasitic flatworms, also expose PS (van der Kleij et al., 2002), as does *Toxoplasma gondii* (Seabra et al., 2004).

PS exposure has also been shown on the exterior cell surface following infection by intracellular bacterial pathogens, such as *Yersinia pestis* and *Francisella tularensis*, which cause plague and tularemia, respectively (Lonsdale et al., 2011). *Listeria monocytogenes* also promotes the release of membrane-derived vesicles with exofacial PS from infected host cells (Czuczman et al., 2014). Similarly, endothelial cells infected with the meningitis-causing pathogen, *Neisseria meningitidis*, exhibited PS translocation to the cell surface (Schubert-Unkmeir et al., 2007). Infection with *Mycobacterium tuberculosis*, which replicates intracellularly in macrophages, is associated with PS externalization in neutrophils in the tubercle lesion (Francis et al., 2014). Likewise, *Legionella pneumophila*, a facultative intracellular parasite, induces PS externalization in human monocytes (Hägele et al., 1998).

Thus, the PS externalization common to the facultative intracellular parasites detailed above is likely to occur for other such pathogens, such as *Salmonella* and *Brucella*. This has also been documented for infection by obligate intracellular parasites, such as *Chlamydia* spp., in which PS externalization is important to pathogenesis and has been shown on infected epithelial, endothelial, granulocytic and monocytic cells (Goth & Stephens, 2001).

Indeed, PS externalization on host cells is now a generally recognized phenomenon in response to infection with a range of bacteria and pathogens (Wandler et al., 2010). This further includes *Helicobacter pylori*, which invades gastric epithelial cells (Petersen & Krogfelt, 2003) and, upon direct contact with those cells, induces externalization of PS to the outer leaflet of the host plasma membrane (Murata-Kamiya et al., 2010).

Prominent pathogens that cause the host cell to externalize PS are viruses (e.g., U.S. Pat. No. 7,790,159; U.S. Pat. No. 7,906,115; Soares et al., 2008; Mercer and Helenius, 2008; Moody et al., 2010; Morizono et al., 2011; Meertens et al., 2012; Best, 2013; Bhattacharyya et al., 2013; Jemielity et al., 2013; Moller-Tank & Maury, 2014). Indeed, the role of PS and PS receptors as enhancers of enveloped virus entry and infection is now well-documented (see, e.g., Table 1 in Moller-Tank & Maury, 2014; and also Example X herein). The connection between extracellular microvesicles such as exosomes and viral infection has also become increasingly apparent in recent years (Meckes & Raab-Traub, 2011; Sims et al., 2014), and again applies to a wide range of viruses (e.g., Walker et al., 2009; Meckes et al., 2010; Izquierdo-Useros et al., 2010; Meckes & Raab-Traub, 2011).

Moreover, the connection between PS, viruses and PS-positive viral-derived extracellular microvesicles is not limited to enveloped viruses, but extends to non-enveloped viruses (Clayson, et al., 1989; Chen et al., 2015). In particular, see the Figure on the cover page of the Cell article by Chen et al., 2015, which shows "PS lipid vesicles" and accompanies the data showing that PS vesicles enable efficient en bloc transmission of enteroviruses.

Figure 10A:
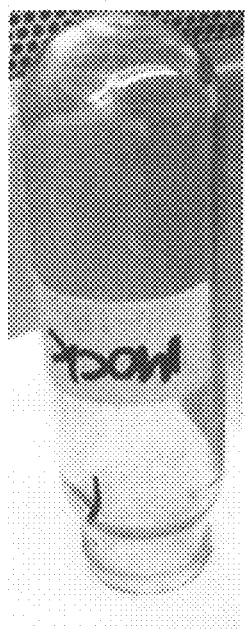
FIG. 10A, FIG. 10B and FIG. 10C. Isolation of extracellular microvesicles such as exosomes from virally-infected cells and viral cultures. Separate populations of Vero cells were mock-infected (negative control.
Figure 10B:
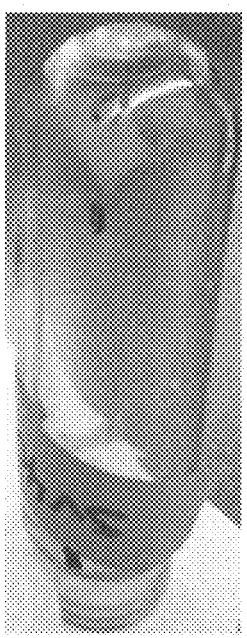
Figure 10C:
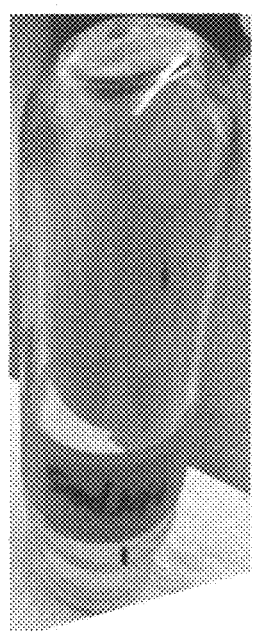

The present invention has been successfully used to isolate extracellular microvesicles such as exosomes from virally-infected cells and viral cultures (Example XI and Example XIII; FIG. 10A, FIG. 10B and FIG. 10C), which are shown to be essentially free from infectious virus (Example XII). Together, those data show the isolation of essentially non-infectious, PS-positive, extracellular microvesicles from cells infected with both enveloped (e.g., HSV-1) and non-enveloped viruses (e.g., SV40).

While not being bound by this, the following comments explain the rationale for the use of the present invention in precipitating extracellular microvesicles from both enveloped and non-enveloped viruses. All viruses orchestrate a timed exit of mature virions from the host cell to ensure successful infection of a new host cell. Enveloped viruses utilize the host cell plasma membrane to embed viral proteins that mediate efficient entry of the progeny virions with the next host cell. PS is found on the exterior of virus infected cells prior to virus release and enveloped viruses incorporate PS into the viral envelope upon exiting the host cell (e.g., Example X).

Viruses that do not incorporate an envelope into their mature virion leave the host cell by other mechanisms. Some strategies non-enveloped viruses use to release new virions from the cell include lysis of the cell, which can be caused directly by the host immune response to the infected cells (T cells or macrophages), or due to the activity of virus directly on host cell protein synthesis or cellular structures. An example of a virus alters the cell structure to induce cell lysis is Adenovirus. Adenovirus expresses several proteins late during infection that alter the structural integrity of the cell by disrupting filament networks and protein synthesis (Flint, 2000). Some non-enveloped viruses are able to release their progeny viruses via a nondestructive mechanism without any cytopathic effect. While poliovirus induces cell lysis rapidly (about 8 hours), it is also released from cells in PS lipid vesicles that are capable of infecting new host cells. Poliovirus particles in PS-vesicles are more efficient in infecting HeLa cells and primary macrophages than virus particles removed from PS-vesicles and blocking the vesicles with Annexin V inhibited the vesicles from infected cells in a dose dependent manner, suggesting the PS lipids are cofactors for poliovirus infection. In addition to poliovirus, Coxsackievirus B3 and Rhinovirus particles are also released into PS lipid vesicles (Chen et al., 2015), indicating a common mechanism utilized by enteroviruses to selectively release mature particles without lysis of the cell.

In regard to SV40 used herein, it is likely that SV40 is also released from cells in the above types of PS-lipid vesicles. Although this has not been published, it has been reported that SV40 particles can be found released from cells before induction of cytopathic effects (Clayson et al., 989). Also, SV40 virions have been observed in cytoplasmic smooth vesicles at 48 hour post infection and the release of SV40 particles was inhibited by monensin, a sodium ionophore that blocks intracellular protein transport by blocking cation transport across lipid membranes.

In other embodiments of the invention, as the use of acetate buffers to isolate extracellular microvesicles such as exosomes is believed to involve surface PS in association with non-lipid membrane components, particularly membrane proteins, and as exosomes and viruses are in the same size-range (e.g., see György et al., 2011), the present invention includes methods and compositions for isolating viruses using acetate buffers. As the use of buffers having a pH of between about 5.25 and about 4.25, including a pH of about 4.75, is likely to inactivate virus due to the relatively low pH, the methods are not currently proposed for isolating infectious viruses. Rather, the methods are more suitable for isolating non-infectious viruses, suitable for use, e.g., in characterization, antigen-typing and related analyses. Possibly, the methods may still be used for isolating infectious viruses, particularly when used towards the higher end of the effective pH range and, more particularly, where a high yield is not necessary or desired. Otherwise, as set forth above, the methods and compositions of the invention are better suited for isolating extracellular microvesicles such as exosomes from viruses, wherein it is an advantage of the invention that it is suitable for isolating viral extracellular microvesicles such as exosomes, substantially free from infectious viruses.

Several other diseases and disorders are known in which the host cells expose PS and/or in which PS-positive extracellular microvesicles and exosomes have been documented. For example, in sickle cell disease and crisis, 30-40% of erythrocytes are prematurely senescent and PS-positive ("sickle erythrocytes"), as opposed to only about 1% in healthy people. The PS-positive sickle erythrocytes remain in circulation, adhere to the endothelium and their exposed PS acts as a platform for the initiation of the coagulation cascade that is responsible for clot propagation (Kennedy et al., 2015).

PS-positive extracellular microvesicles are also released from atherosclerotic plaques (Mallat et al., 1999). Both Type 1 and Type 2 diabetic patients have PS-positive extracellular microvesicles, as shown by being annexin V-positive (Sabatier et al., 2002). In Alzheimer's disease, brain exosomes contain PS and amyloid β-peptide (Aβ), the pathogenic agent of the disease (Yuyama et al., 2012). PS-positive extracellular microvesicles are also involved in sepsis, where they are markers and mediators of sepsis-induced microvascular dysfunction and immunosuppression (Souza et al., 2015). The present invention can thus be applied to isolating PS-positive extracellular microvesicles from all such diseases and disorders.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Isolating Tumor-Derived Exosomes Using Acetate Buffers

The present example shows advantageous methods for isolating extracellular microvesicles such as exosomes, particularly tumor-derived exosomes, using acetate buffers.

A. Materials and Methods

The following Materials and Methods are relevant to the results reported in Example I, Example II and Example III.

1. Tissue Culture

K1735P murine melanoma (tumor) cells (provided by I. J. Fidler, M. D. Anderson Cancer Center, Houston, Tex., but anyway widely available) were cultured in minimal essential media (MEM) supplemented with L-glutamine (2 mM), Na pyruvate (1 mM), penicillin (100 U/mL), streptomycin (100 µg/mL), nonessential amino acids and fetal bovine serum (10%). Cells (about $25 \times 10^6$ in 15 mL media) were seeded into the lower chamber of CELLine AD 1000 flasks (Integra Biosciences AG) that contained 250 mL media in the upper chamber (Mitchell et al., 2008). Conditioned media (about 15 mL) was collected from the lower chamber weekly. The compartment was washed once with 15 mL of phosphate-buffered saline (PBS) and combined with the conditioned media. Fresh media was then added to the lower chamber. The upper chamber was replenished weekly by replacing about 100 mL spent media with fresh media. Weekly collections were subjected to the acetate buffer precipitation protocol and typically yielded 75-125 µg of purified exosomes/mL of conditioned media (see results below).

2. Isolation of Tumor-Derived Exosomes

Ultracentrifugation—Cell conditioned media was cleared of cells, cell debris and large membrane vesicles by sequential centrifugation at 500 g for 30 min followed by 12,000 g for an additional 30 min. Exosomes were collected from the cleared supernatants after ultracentrifugation at 100,000 g for 1 hr. The pellets were resuspended in about 2 mL HEPES-saline (HBS; NaCl 150 mM, HEPES 20 mM, EGTA 2 mM, pH 7.6). Exosome quantity was estimated by BCA protein assay.

Acetate buffer precipitation protocol (standard)—Cell conditioned media was cleared of cells, cell debris and large membrane vesicles by sequential centrifugations. The cell conditioned media was centrifuged at 500 g for 30 min (or 250 g for 10 min) and the supernatant was collected and then centrifuged at 12,000 g to 13,000 g for an additional 30 min. These steps provide a cleared or clarified supernatant. A solution of 1.0 M sodium acetate in water was prepared and titrated to pH 4.75 with glacial acetic acid and $\frac{1}{10}^{th}$ volume of this Na acetate buffer was mixed with the cleared supernatants and left on ice for 30-60 min. Typically, the mixture was then transferred to 37° C. for an additional 5 min (although this is optional). The resulting turbid suspension was centrifuged for 10 min at 2,000 g to 5,000 g, typically at 5,000 g, the supernatant discarded, and the resulting pellet was washed once with 0.1M Na acetate buffer. The resuspended pellet was again centrifuged at about 2,000 g for 10 min and the final pellet "solubilized" in hepes-buffered saline (HBS) or TRIS-buffered saline (TBS), as examples of acetate-free buffers. Optionally, any remaining insoluble material can be removed by centrifugation at about 2,000 g for 10 min and/or still further purification was achieved by an additional round of precipitation. The purified exosomes were stored at 4° C.

3. Flow Cytometry

Tumor exosomes (10 µg protein) in 0.5 mL PBS were mixed overnight at 4° C. with 5 µL of 4 µM aldehyde-activate latex beads (4% w/v) (Invitrogen). The beads were then blocked by adding 0.5 mL of 1% bovine serum albumin (BSA) for 1 hr followed by 0.1 mL of 100 mM glycine for an additional hour. The beads were then washed and resuspended in PBS. Antibodies included rabbit anti-alix (sc-99010; Santa Cruz) and rabbit anti-tubulin (sc-5546; Santa Cruz) as an isotype control followed by CY3-labeled donkey anti-rabbit Ig. The primary antibody was incubated with the beads for 1 hr on ice, washed twice, followed by an additional 1 hr with the labeled secondary. The beads were again washed and analyzed. Fluorescein isothiocyanate (FITC)-annexin 5 (BD Biosciences) was used as described by the manufacturer. Samples included BSA-blocked beads and exosome-beads incubated with annexin 5 in the presence and absence of $Ca^{2+}$ (1 mM).

4. Electron Microscopy

Isolated exosomes were prepared for examination by transmission electron microscopy using a procedure slightly modified from that described by Thery et al., 2006. Briefly, 25 µl of exosome suspension was place on parafilm and carbon-coated grids were suspended, face down, on the suspension for 1 min. The grids were then washed by three sequential passages for 1 min each on water. The grids were then stained by placing them on a 25 µl droplet of 2% uranyl acetate for 1 min and again washed in water as described above. Excess water was removed by blotting on filter paper. The grids were then air dried for several min. Samples were examined with a JEOL 1200 EX electron microscope.

5. Gel Electrophoresis and Western Blotting

Exosomes were solubilized at 95° C. for 5 min in an equal volume of Laemmli sample buffer (Bio-Rad) containing 5% β-mercaptoethanol. Aliquots (20 µg protein) were subjected to electrophoresis through duplicate 'Ready Cast' 10% acrylamide gels (Bio-Rad). One gel was stained with Coomassie blue and the duplicate was transferred to PVDF membranes overnight at 4° C. The membranes were blocked with 5% non-fat milk in TRIS-buffered saline (TBS) containing 1% Tween-20. The indicated primary antibodies (anti-alix, anti-hsp70; Santa Cruz), were added for 1 hr followed by three washes with TBS. Antibody binding was assessed with appropriate HRP-conjugated secondary antibodies and visualized by enhanced chemoluminescence.

B. pH and Concentration Ranges

Tumor cell cultures were established in the highly efficient CELLline AD tissue culture system (Mitchell et al., 2008). Supernatants were retrieved from the lower, cell-containing chamber and intact cells and cellular debris were removed by centrifugation at 500 g and 12,000 g, respectively. Small (4.5 mL) aliquots of the clear supernatants were then mixed with $\frac{1}{10}^{th}$ volume of increasing 10× acetate concentrations titrated to the indicated pH with acetic acid.

FIG. 1A and FIG. 1B show the effective isolation of tumor-derived exosomes across this range of acetate buffers. It can be seen that the entire range of salt and pH conditions were effective in precipitating tumor exosomes, with meaningful levels of protein being recovered from all the test conditions. It should also be noted that this study was designed to readily provide a wide range of comparative data and was not designed with any attempt to optimize yield. Under the range of effective conditions, precipitation was essentially instantaneous and clearly visible (e.g., as shown in FIG. 1C using pH 4.75 with 0.1M acetate).

By fitting the curves to the data points, it can be seen from FIG. 1A that acetate buffers across the entire range of salt and pH conditions are effective in precipitating tumor exosomes, including from pH 3.75 to pH 5.75, and from 0.05M to 0.5M. The actual data points show that, across the full range of concentrations from 0.05M to 0.5M, effective precipitation occurred at pH 4.14, pH 4.39, pH 4.64, pH 4.89, pH 5.14 and pH 5.64 (FIG. 1A). Effective precipitation also occurred at each concentration tested, namely 0.05M, 0.1M, 0.233M, 0.367M and 0.5M (FIG. 1A). By fitting the curves to the data points, the pH optimum for each concentration can be determined as follows: pH 4.65 at 0.05M; pH 4.75 at 0.1M; pH 4.80 at 0.233M; pH 4.77 at 0.367M; and pH 4.78 at 0.5M (FIG. 1B).

However, despite acetate buffers across the entire ranges of pH and concentration being effective, this "salting-out" or precipitation method was influenced by both pH and salt concentration. FIG. 1A shows that ranges of between about pH 4.14 and about pH 5.25 or between about pH 4.25 and about pH 5.25, and more particularly, between about pH 4.5 and about pH 5.0, and concentrations of between about 0.05M and 0.25M, and more particularly, between about 0.05M and 0.1M acetate are most effective. Using space-filling (or 3D) models of these same data, ranges of between about pH 4.14 and about pH 5.25, between about pH 4.14 and about pH 5.0, between about pH 4.39 and about pH 5.4, between about pH 4.39 and about pH 5.25 and between about pH 4.39 and about pH 5.14, and concentrations of between about 0.05M and 0.25M, between about 0.05M and 0.233M and between about 0.05M and 0.15M, and more particularly, between about pH 4.5 and about pH 5.4, between about pH 4.5 and about pH 5.25 and between about pH 4.5 and about pH 5.0, and concentrations of between about 0.05M and 0.233M, between about 0.05M and 0.15M and between about 0.05M and 0.1M are most effective.

From FIG. 1A and space-filling models of the same data, preferred ranges are between about pH 4.5 and about pH 5.25, or between about pH 4.5 and about pH 5.0, and concentrations of between about 0.05M and 0.15M, or between about 0.05M and 0.1M. Within these effective ranges, maximal precipitation in these studies with 0.1M acetate occurred at about pH 4.75. This was therefore chosen as a convenient standard condition for future studies, including those below and reported in the subsequent Examples.

C. Yield

Starting with about 25×10$^6$ K1735P cells, culturing under the conditions described above for two weeks before the first collection of conditioned media, and performing the acetate precipitation as described above (and using 0.1M sodium acetate at pH 4.75), a yield of about 75-125 μg of purified exosomes per mL of conditioned media is obtained. Maintaining these cells in culture and replenishing spent media with fresh media, as described above, provides a constant source of so-called "fully saturated" cell conditioned media (albeit from a then unknown number of cells), from which about 75-125 μg/mL, and typically about 100-125 μg/mL, of purified exosomes can be obtained weekly using the acetate buffer precipitation protocol.

As noted, the data in FIG. 1A and FIG. 1B were generated from small samples to show a comparison of conditions and not with a view to depict typical yields. It has been observed that the % yield increases when using the fully saturated media, as opposed to less concentrated small samples.

Example II

Further Characterization of Tumor Exosome Isolation

This example further characterizes the isolation methodology for disease-related extracellular microvesicles such as exosomes, and highlights the importance of acetate buffers in the technique with reference to tumor exosomes.

A. Temperature Independence

The present study shows that tumor exosome precipitation is essentially temperature-independent. However, analyzing the effect of temperature showed that the development of turbidity was temperature-dependent.

Figure 2A:
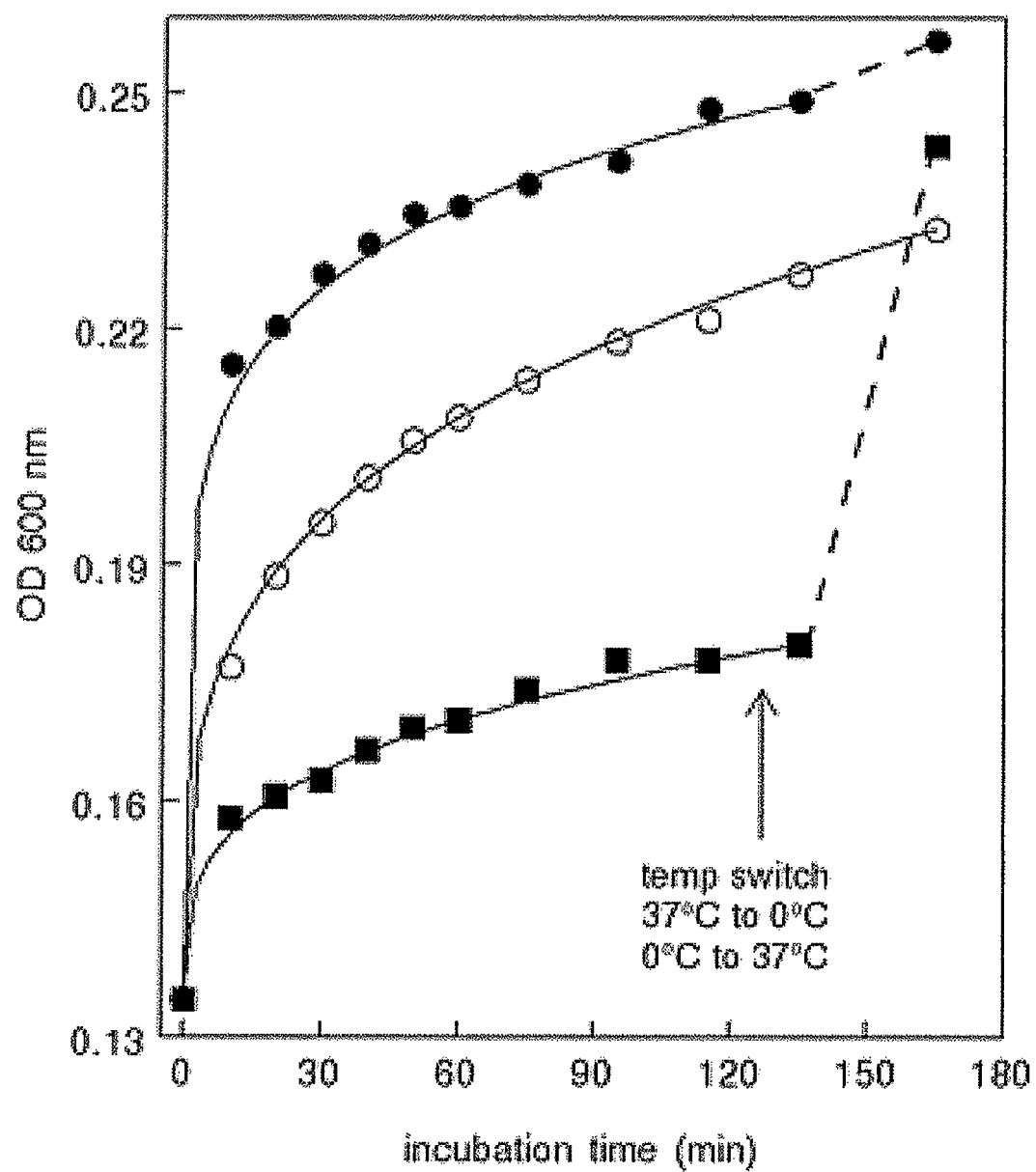
FIG. 2A and FIG. 2B. Temperature dependence of tumor exosome isolation.
Figure 2B:
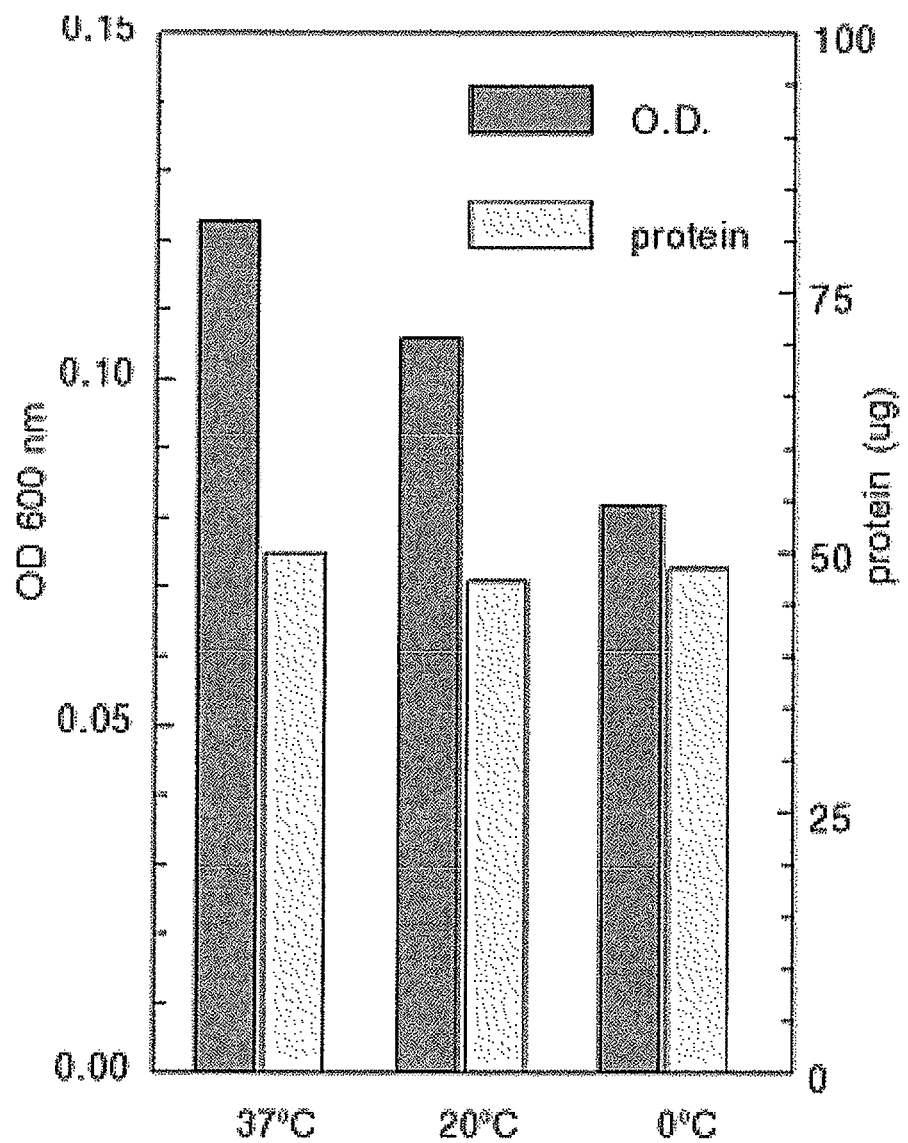

An immediate temperature-dependent increase in turbidity occurred upon the addition of acetate, which then began to level off. Continued incubation showed a modest, about 2-fold increase in rate between 0° C. and 20° C. However, no significant difference in rate was observed upon increasing the temperature from 20° C. to 37° C. (FIG. 2A). Interestingly, once the reaction plateaued at 0° C., increasing the temperature to 37° C. resulted in an immediate increase in turbidity to levels that approached that of samples incubated for the entire period at 37° C. (FIG. 2A). Conversely, decreasing the temperature of samples incubated at 37° C. was without effect (FIG. 2A).

Irrespective of turbidity, the amounts of protein recovered in the pelleted precipitates were essentially identical (FIG. 2B), indicating that tumor exosome precipitation is temperature-independent, with larger aggregates being formed at higher temperatures.

B. pH Dependence

To further assess the pH dependence of tumor-derived exosome precipitation, spent media and cleared cell supernatants from the same Integra flasks were incubated for 1 hr in 0.1M Na acetate buffers. Turbidity was assessed at 600 nm and precipitated protein (exosomes) was assessed by Bradford assay.

Figure 3A:
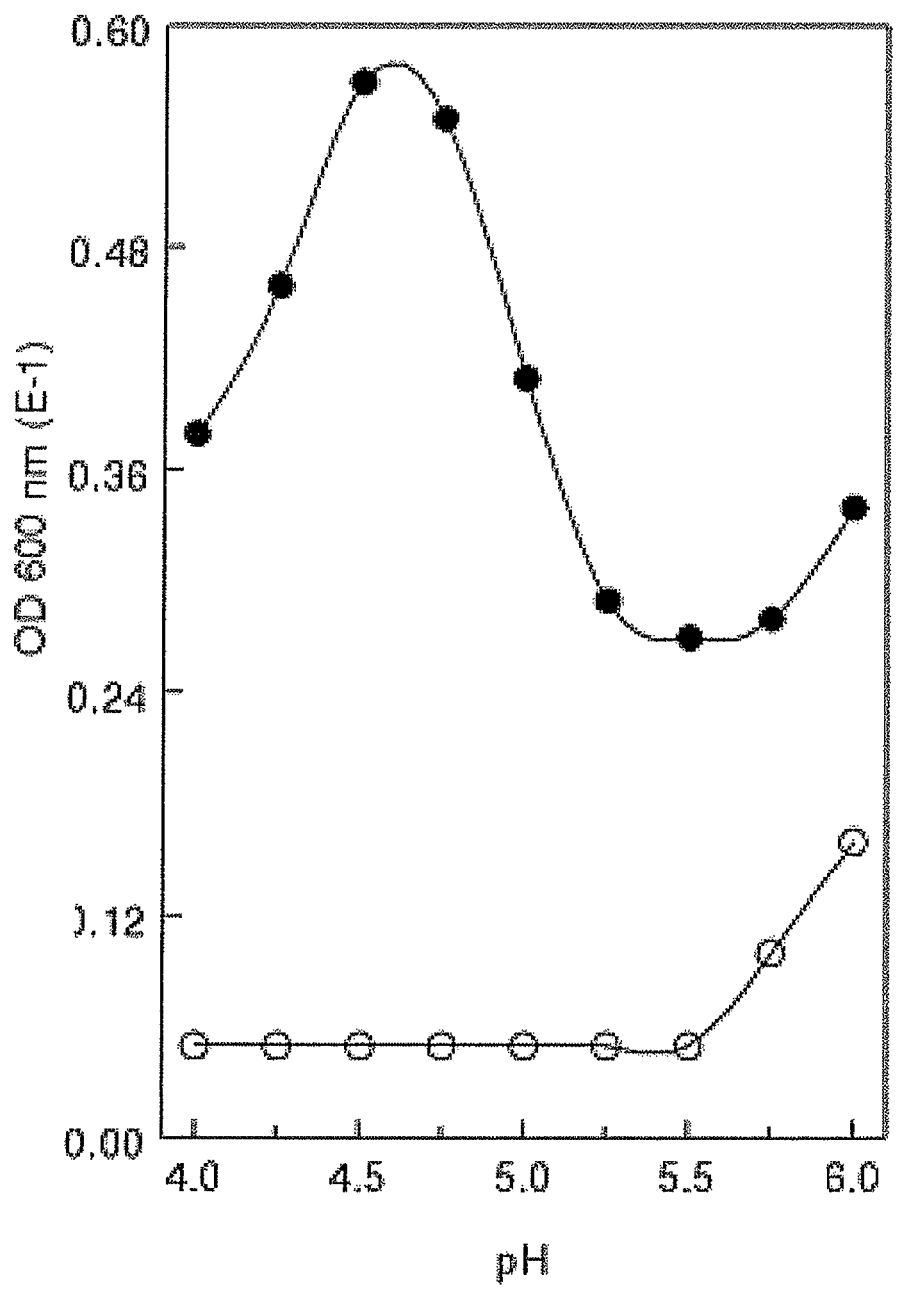
FIG. 3A and FIG. 3B. Differential isolation of tumor exosomes from cell supernatants and spent media. Aliquots from the CELLine flasks lower (●, cells) and upper (○, media) chambers were pre-cleared and mixed with 1/10th volume of 1.0M acetate at the indicated pH. After incubation for 1 hr on ice, turbidity (FIG. 3A) was assessed at 600 nm and protein (FIG. 3B) in re-solubilized centrifuged (5,000 g; 10 min) pellets.
Figure 3B:
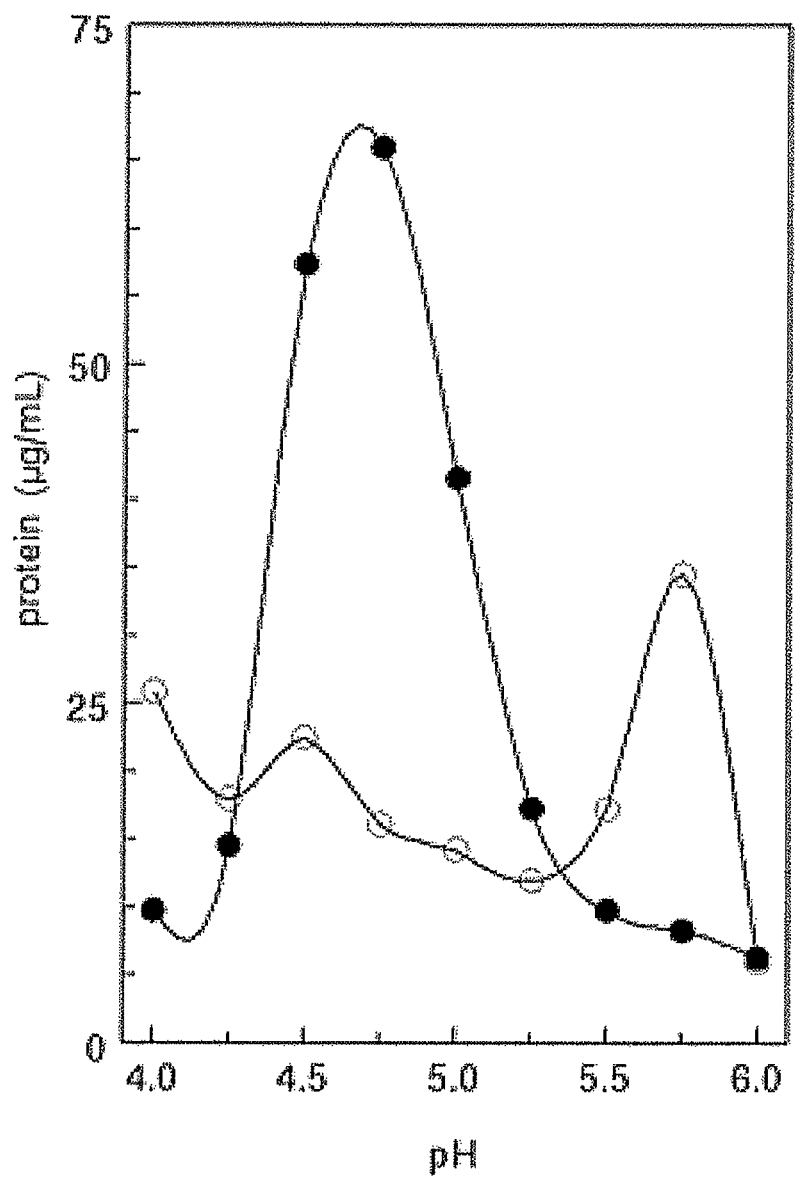

As shown in FIG. 3A and FIG. 3B, pH-dependent turbidity (FIG. 3A) and precipitated protein (FIG. 3B) were obtained with the supernatants, whereas essentially no turbidity or precipitate was observed with the control media. Within the effective pH range, maximum turbidity and precipitated protein from the supernatants in this study were again obtained at about pH 4.75.

C. Precipitation is Dependent on Acetate, not pH

Figure 4A:
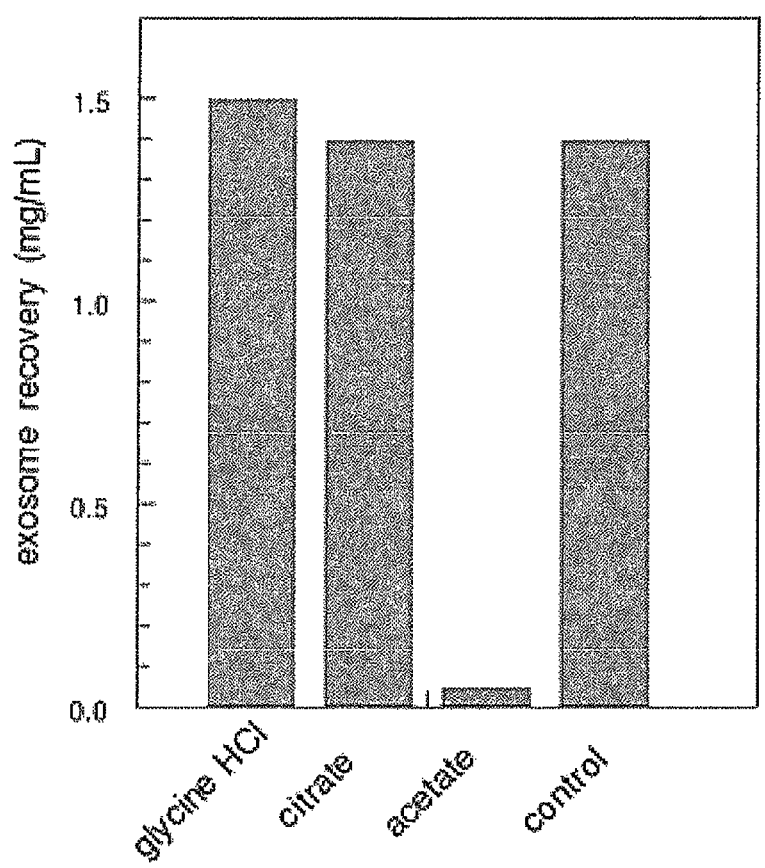
FIG. 4A and FIG. 4B. Acetate causes the tumor exosomes to precipitate.

The importance of acetate, rather than pH itself, in precipitating tumor-derived exosomes is shown by these acidification studies. Precipitation was found to be dependent on the presence of acetate, not just acidification, since precipitation did not occur with supernatants acidified with glycine HCl or citrate (FIG. 4A).

D. Precipitation is Dependent on Acetate, not the Counter Ion

Although tumor exosome precipitation is dependent on the presence of acetate, the standard sodium acetate can be substituted with other acetate buffers, such as potassium acetate or ammonium acetate. The irrelevance of the counter ion is shown by these controlled studies, in which precipitation by potassium acetate is shown to be equivalent to precipitation by sodium acetate.

4T1 breast carcinoma cells were cultured in CELLline AD tissue culture system. Supernatants were retrieved from the bottom, cell-containing chamber and media was obtained from the top chamber, which is separated from the bottom cell chamber via a dialysis membrane. Equal volume samples of supernatants from the bottom chamber and media from the top chamber were separately mixed with $\frac{1}{10}^{th}$ volume of 10× sodium acetate or 10× potassium acetate at about pH 4.75 and left for 30 mins.

Figure 4B:
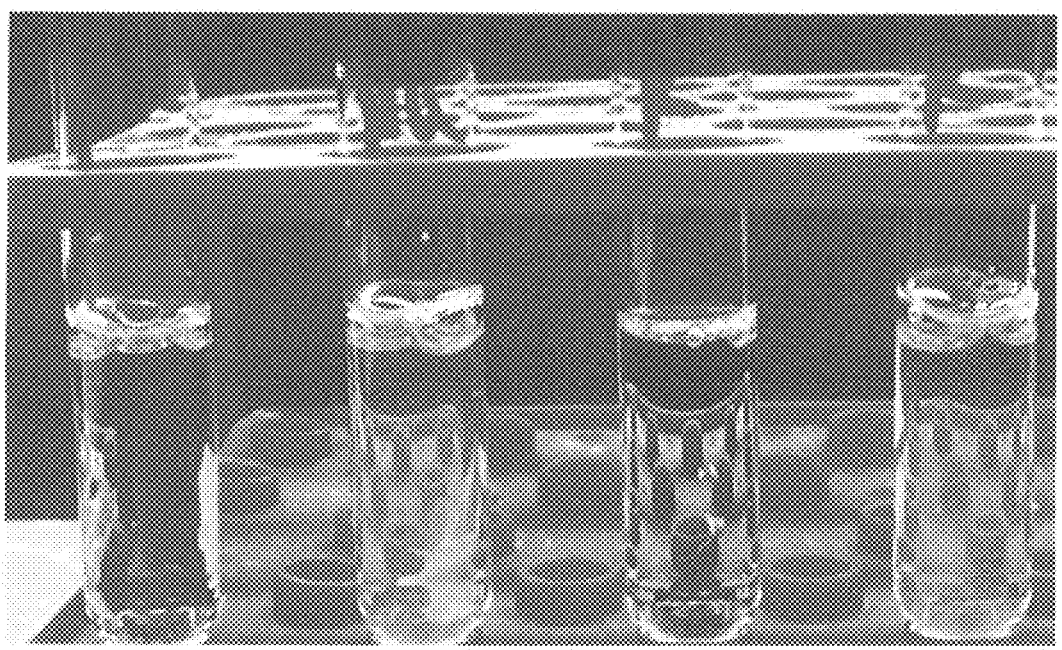

FIG. 4B shows that the use of potassium acetate is indistinguishable from the use of sodium acetate. Using these two acetate buffers, precipitation of exosomes from the supernatant from the bottom chamber was clearly visible and equivalent. As expected, no precipitation from the media from the top chamber was observed with either acetate buffer, as exosomes are maintained in the bottom cell chamber, being too large to pass through the dialysis membrane. The clearly visible turbid suspensions were centrifuged and produced pellets of exosomes that were visibly indistinguishable between the potassium acetate and the sodium acetate.

Example III

Equivalent Yield of Morphologically Verified Tumor Exosomes

The present example shows that the yield of disease-related extracellular microvesicles such as exosomes isolated using acetate buffers is equivalent to that from the typical ultracentrifugation method, even though the acetate method is easier and quicker. The acetate-purified exosomes, as exemplified by tumor exosomes, are also shown to be morphologically indistinguishable from those prepared by traditional ultracentrifugation and to be antigenically intact.

A. Equivalent Yield

Figure 5A:
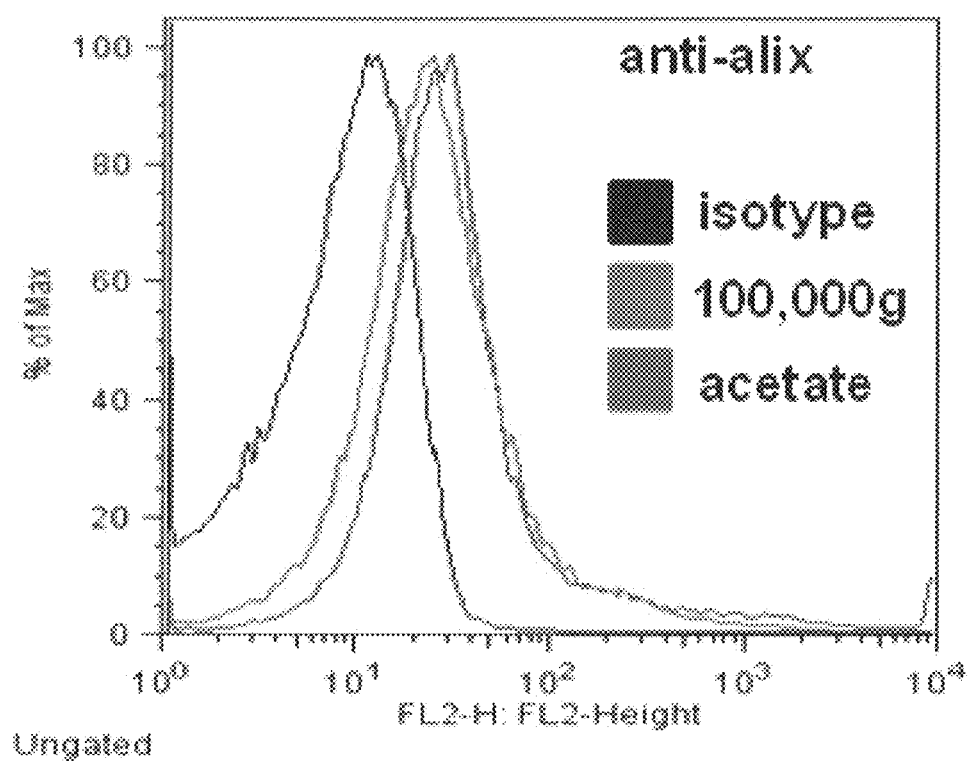
FIG. 5A and FIG. 5B. Comparative yields of tumor exosomes isolated with acetate vs. 100,000 g ultracentrifugation. 50 mL of pre-cleared cell supernatant was centrifuged at 100,000 g for 1 hr or at 5,000 g for 10 min after 60 min incubation with acetate. The pellets were resuspended in HBS. Flow analysis of exosomes stained with alix antibodies (FIG. 5A; isotype control, black (left) line; 100,000 g, red (middle) line; acetate, blue (right) line) and annexin 5 (FIG. 5B; no $Ca^{2+}$, black (left most) line; 100,000 g, red line; acetate, blue line) is shown (the curve for the red line extends to the left and right of the curve for the blue line).
Figure 5B:
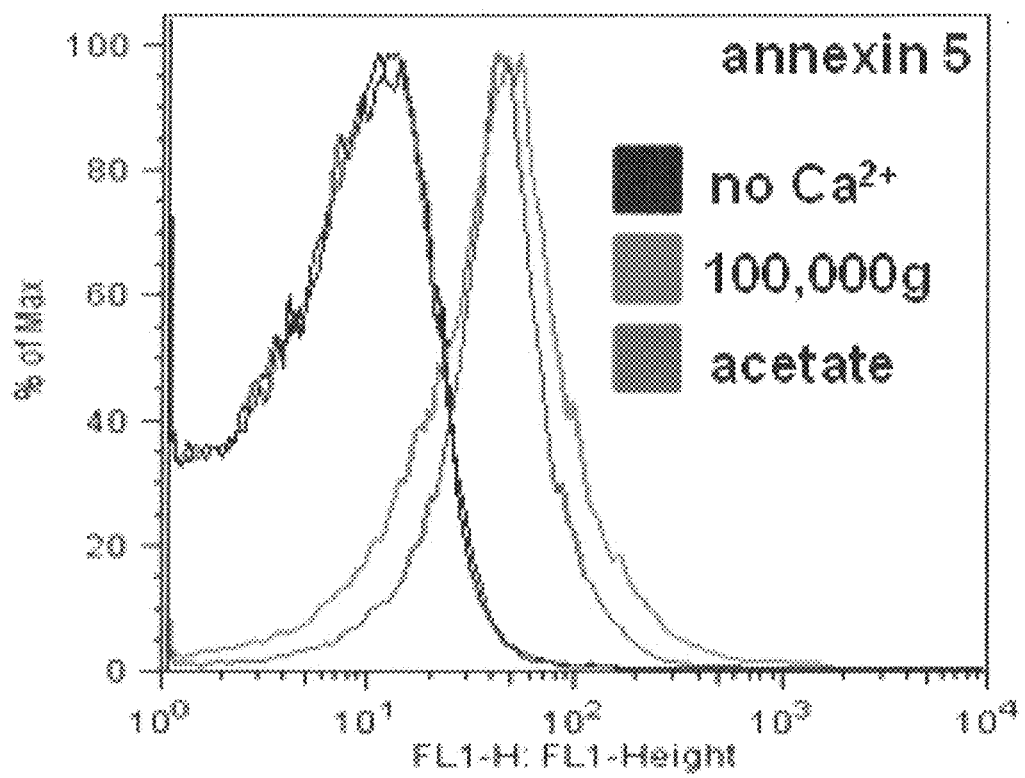

The relative yield of tumor exosomes obtained with acetate isolation and with conventional 100,000 g ultracentrifugation was quantified by assessing alix and PS in both populations. Flow cytometry analysis of alix with Cy3-labeled alix antibodies (FIG. 5A) and PS with FITC-labeled annexin 5 (FIG. 5B) suggested that both methods yielded similar amounts of exosomes.

In directly comparing the yield of protein obtained with acetate isolation and with conventional 100,000 g ultracentrifugation, identical aliquots of K1735 supernatants were isolated by both methods. In addition, the supernatants from the 100,000 g ultracentrifugation and acetate protocols were subjected to an additional round of isolation by acetate pH 4.75 and ultracentrifugation (after bringing the solution to pH 7.5), respectively.

The protein yield with the acetate protocol was about 2-fold higher than the ultracentrifugation method (167.0 µg/ml vs. 88.1 µg/ml). Additional protein could not be recovered after ultracentrifugation of neutralized acetate supernatants, suggesting that virtually all the exosomes were precipitated with acetate. On the other hand, acetate treatment of the 100,000 g ultracentrifugation supernatants recovered an additional 533 µg of protein (39.5 µg/ml), suggesting that the acetate could have non-specifically precipitated non-exosomal proteins. SDS-PAGE of exosomes recovered from acetate precipitation and 100,000 g precipitation showed similar protein patterns, with the exception of an additional band at the top of the acetate lane. Mass spectroscopy analysis indicated that this upper band (about 160 kDa) in the acetate sample was α2-macroglobulin, a protein known to be secreted by some melanoma cells (Morgan et al., 1984).

In separate studies using acetate precipitation to purify exosomes from B16 melanoma or TRAMP prostate carcinoma cells, α2-macroglobulin was not detectable in the resultant exosomes (Example IV).

As to the higher concentration of α2-macroglobulin in the acetate-precipitated exosomes from K1735 cells, which is likely the result of acid-dependent co-precipitation unrelated to the precipitation of exosomes, this can be easily removed by washing the neutralized acetate-precipitated exosomes once at 100,000 g. Indeed, SDS-PAGE of the washed exosomes revealed that most of the α2-macroglobulin was removed.

B. Morphologically Indistinguishable Exosomes

Figure 6:
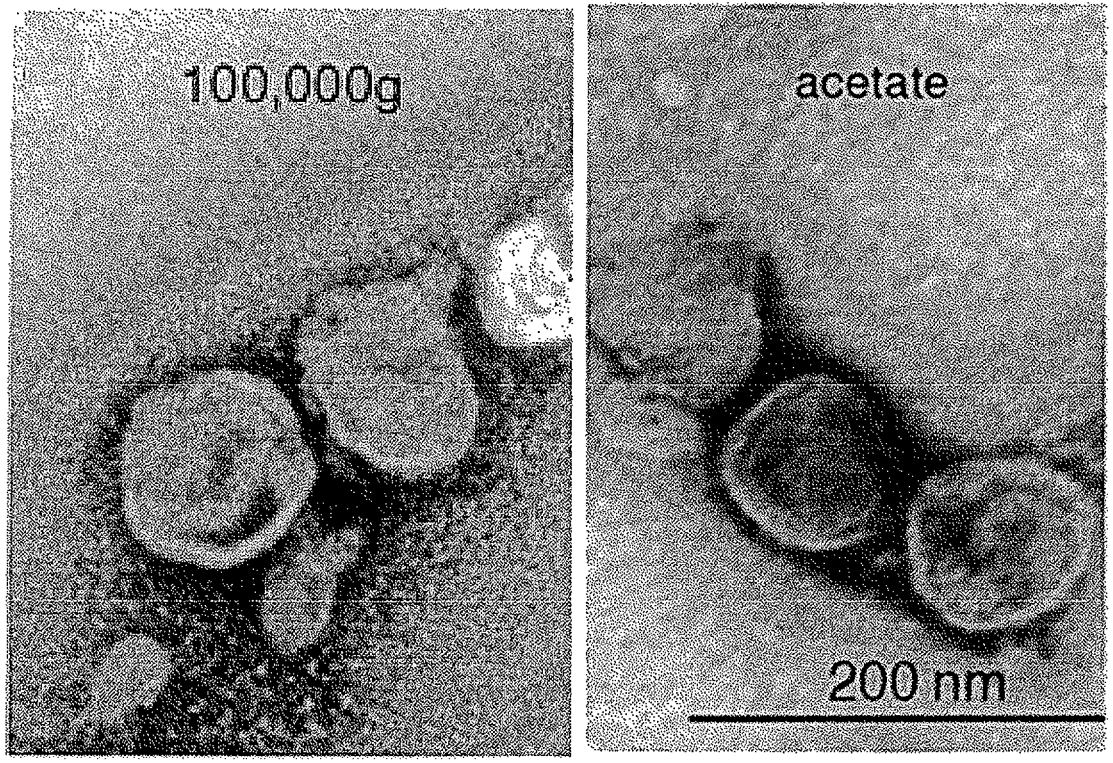
FIG. 6. Characterization of tumor exosomes. Negatively-stained melanoma-derived exosomes purified by 100,000 g ultracentrifugation or with acetate were visualized by transmission electron microscopy.

Tumor exosomes purified with acetate and by traditional ultracentrifugation were analyzed by electron microscopy, and by western blotting for characteristic exosome-associated markers. It was determined that exosomes recovered with acetate were morphologically indistinguishable from exosomes collected by ultracentrifugation. Both populations contained vesicles of identical size and had typical bilayer membranes enclosing a luminal space (FIG. 6).

Western blot analysis confirmed that both preparations contained the exosome markers alix and hsp70. Binding to antibodies in the western blot therefore shows the isolated exosomes to be antigenically intact.

Example IV

Isolating Exosomes From Deposited Tumor Cell Lines

In this example, acetate precipitation has been used to purify disease-related extracellular microvesicles, particularly tumor exosomes, from additional tumor cell lines. These include tumor cell lines that are deposited with the American Type Culture Collection (ATCC®), and are therefore readily available as a standard for comparative studies.

4T1 breast carcinoma cells are available from ATCC as CRL-2539™. B16 melanoma cells are available from ATCC as B16-F0 (ATCC® CRL-6322™), B16-F1 (CRL-6323™) and B16-F10 (CRL-6475™). TRAMP cells, which are transgenic mouse prostate carcinoma cells, are available from ATCC as CRL-2730™, CRL-2731™ and CRL-2732™. C4 cells are androgen-sensitive human prostate adenocarcinoma cells from an LNCaP cell line (Wu et al., 1994) and are widely available.

4T1, B16 and TRAMP cells, each obtained from ATCC, and C4 cells were separately cultured in minimal essential media (MEM) supplemented with L-glutamine (2 mM), Na pyruvate (1 mM), penicillin (100 U/mL), streptomycin (100 µg/mL), nonessential amino acids and fetal bovine serum (10%). About 25×10$^6$ of each cell type (4T1, B16, TRAMP and C4) in 15 mL media were seeded (day 0) into the lower chamber of CELLine AD 1000 flasks (Integra Biosciences AG) that contained 250 mL media in the upper chamber (Mitchell et al., 2008). Starting at two weeks after seeding, conditioned media (about 15 mL) was collected from the lower chamber and the collection was continuing weekly thereafter. Each time, the compartment was washed once with 15 mL of phosphate-buffered saline (PBS) and combined with the conditioned media. Fresh media was then added to the lower chamber. The upper chamber was replenished weekly by replacing about 100 mL spent media with fresh media.

The collected conditioned media (about 30 mL total when combined with the PBS wash) was cleared of cells, cell debris and large membrane vesicles by sequential centrifugations. That is, the cell conditioned media was first centrifuged at 500 g for 30 min (or 250 g for 10 min) and the supernatant was collected; that supernatant was then centrifuged at 12,000 g to 13,000 g for an additional 30 min. These steps provide a cleared or clarified supernatant.

By culturing about $25 \times 10^6$ 4T1, B16, TRAMP, C4 (or K1735P) cells under the above conditions, collecting about 30 mL total of conditioned media (when combined with the PBS wash) after about two weeks of culture, and/or at weekly intervals thereafter, precipitating the cleared supernatants by mixing with $1/10^{th}$ volume of sodium acetate buffer (1.0 M; pH 4.75) on ice for about 30-60 min, and centrifuging once or twice at 2,000 g to 5,000 g for 10 min, the present invention provides a substantially purified exosome population with a protein concentration of about 75-125 µg/mL.

This protocol has been used successfully on K1735P, 4T1, B16, TRAMP and C4 tumor cells. The tumor exosomes purified from such cells were also analyzed by FACS and shown to be positive for phosphatidylserine, as described in detail in Example VII and Example IX.

As at least the 4T1, B16 and TRAMP cells are deposited with the ATCC, these cells can therefore be used as a standard for comparative studies using the protocol described. In using acetate precipitation to purify tumor exosomes from B16 and TRAMP cells, $\alpha$2-macroglobulin was not detected in the resultant exosomes (in contrast to K1735 cells). As B16 and TRAMP cells are deposited with the ATCC, and use of the acetate precipitation method results in purified exosomes essentially free from extraneous or contaminating proteins, B16 and TRAMP cells are considered to be particularly useful as a Reference Example or standard for comparative studies using the acetate precipitation method of the present invention.

Example V

Isolation of Human Tumor Exosomes

This example provides data to confirm that the use of acetate buffers is effective in isolating human disease-related extracellular microvesicles such as exosomes, particularly tumor-derived exosomes from human patients.

A. Human Tumor Exosomes from Tissue Culture

Exosomes were isolated from tissue culture supernatants obtained from human tumor cells. Human ovarian carcinoma cells isolated from ascitic fluid were cultivated in the lower cell chamber of CELLine AD1000 flasks. Conditioned media from the lower cell-containing compartment was collected weekly. The exosome-containing media was cleared of cells, cell debris and large membrane vesicles by sequential centrifugations at 500 g and 12,000 g, respectively. $1/10^{th}$ volume of Na acetate buffer (1.0 M; pH 4.75) was mixed with the cleared supernatants and left on ice for 30-60 min and then transferred to 37° C. for an additional 5 min. The turbid suspension was centrifuged for 10 min at 5,000 g and the resulting pellet was washed once with 0.1M Na acetate buffer. The suspension was again centrifuged and the pellet "solubilized" in hepes-buffered saline containing 2 mM EGTA at pH 7.5. The purified exosomes were stored at 4° C.

B. Human Tumor Exosomes from Patients

Exosomes were also isolated from the ascites fluid obtained from human patients with ovarian carcinoma. Ascitic fluid (up to ~500 mL) was centrifuged at 500 g and 12,000 g to remove cells and cellular debris. $1/10^{th}$ volume of Na acetate buffer (1.0 M; pH 4.75) was added to ice-cold cleared ascites fluid for 30 min to 1 hour. Precipitated exosomes were collected by centrifugation (5,000 g for 15 min). Depending on the donor, yields were in the range of 30 to 50 µg/mL fluid.

Example VI

Tumor Exosome Isolation From Blood Samples

The present example shows that the use of acetate buffers can also be applied to the isolation of disease-related extracellular microvesicles such as exosomes from whole human blood, as exemplified by isolating tumor exosomes.

2.5 mL of whole human blood collected in EDTA was mixed with 0.5 mL of purified tumor exosomes at 1.0 mg/mL (0.5 mg total). The blood was then centrifuged and the plasma collected. Half the plasma was kept on ice and the other half was heated to 56° C. for 3 min to precipitate fibrinogen. Both samples were centrifuged at 500 g for 10 min and the supernatants were collected. $1/10^{th}$ volume of Na Acetate buffer (1.0 M at pH 4.75) was added. After incubating the samples at 0° C. for 60 min, the samples were centrifuged at 500 g for 15 min and exosomes in the pellet were solubilized in hepes-buffered saline containing 2 mM EGTA at pH 7.5 and the protein quantified.

In this study of exosome recovery from whole blood doped with 500 µg tumor exosomes, the total protein recovery from whole plasma was 340 µg, which includes tumor exosomes and acetate-precipitated fibrinogen. The total protein recovery from heated, fibrinogen-free plasma was 201 µg, which represents the total, corrected tumor exosome recovery. This shows that about 40% of the tumor exosomes are recovered (201 µg from the 500 µg doped exosomes).

In another study, purified exosomes were added directly to cell-free plasma and the protocol described above was repeated, but adding 260 µg of purified tumor exosomes. The protein recovery from whole plasma was 405 µg, which includes tumor exosomes and acetate-precipitated fibrinogen. The protein recovery from heated, fibrinogen-free plasma showed essentially 100% tumor exosome recovery (the actual value was 288 µg protein, which is within experimental error for this initial study and/or could indicate precipitation of additional plasma proteins).

These studies show that the difference in the amount of protein recovered is largely due to precipitation of fibrinogen in the plasma samples. Indeed, the removal of the fibrinogen by the pre-incubation step (56° C. for 3 min; Millar et al., 1971; Marx et al., 2008) reduced the levels of extraneous protein in the acetate precipitated samples to levels comparable to those obtained for the serum samples, with essentially no loss of exosomes. As discussed in Example III in regard to $\alpha$2-macroglobulin, any extraneous proteins in the tumor exosome preparation can be easily removed by ultracentrifugation once volumes have been reduced to manageable volumes with acetate.

Example VII

Selective Isolation of Tumor-Derived Exosomes

This example shows the specificity of acetate buffers to precipitate disease-related extracellular microvesicles such as exosomes, as exemplified by tumor-derived exosomes, as opposed to exosomes from normal cells. This provides for important new uses in laboratory techniques and for diagnostic tests and kits.

Ovarian carcinoma (tumor) cells obtained from a human patient and normal mesothelial cells from the same patient were maintained in tissue culture. In this initial study, exosomes were recovered from the respective tissue culture supernatants by one step of ultracentrifugation for 1 hr at 100,000 g. The ultracentrifugation pellets contained spun-down exosomes and residual tissue culture media.

The ultracentrifugation pellets were resuspended in saline and protein was quantified by the Bradford assay. Aliquots from each of the resuspended materials were set aside to assess the presence of phosphatidylserine (PS) on the exosome surface by FACS analyses with FITC-labeled annexin 5, a specific PS marker. Separate aliquots from each of the resuspended materials were then treated with acetate buffer (0.1 M, pH 4.75) for 1 hr at 0° C. The acetate-precipitated pellets were resuspended in saline to the initial volume and protein was again quantified by the Bradford assay. The results are depicted in Table 1.

TABLE 1

Acetate Precipitation of Exosomes from Tumor and Normal Cells

| Source of Cells | Recovery after acetate treatment (%) |
|---|---|
| Ovarian carcinoma cells | 38.7 |
| Normal mesothelial cells | 1.4 |

As shown in Table 1, the acetate buffer specifically precipitates the tumor-derived exosomes from the ovarian carcinoma cells, with virtually no exosomes from the normal cells being recovered. It should also be noted that, because only one ultracentrifugation step was used in this initial study, the exosome suspension contained residual tissue media. Since the acetate precipitation protocol is tumor exosome-specific, the % recovery quoted for the ovarian carcinoma cells is an under-estimation.

Figure 7A:
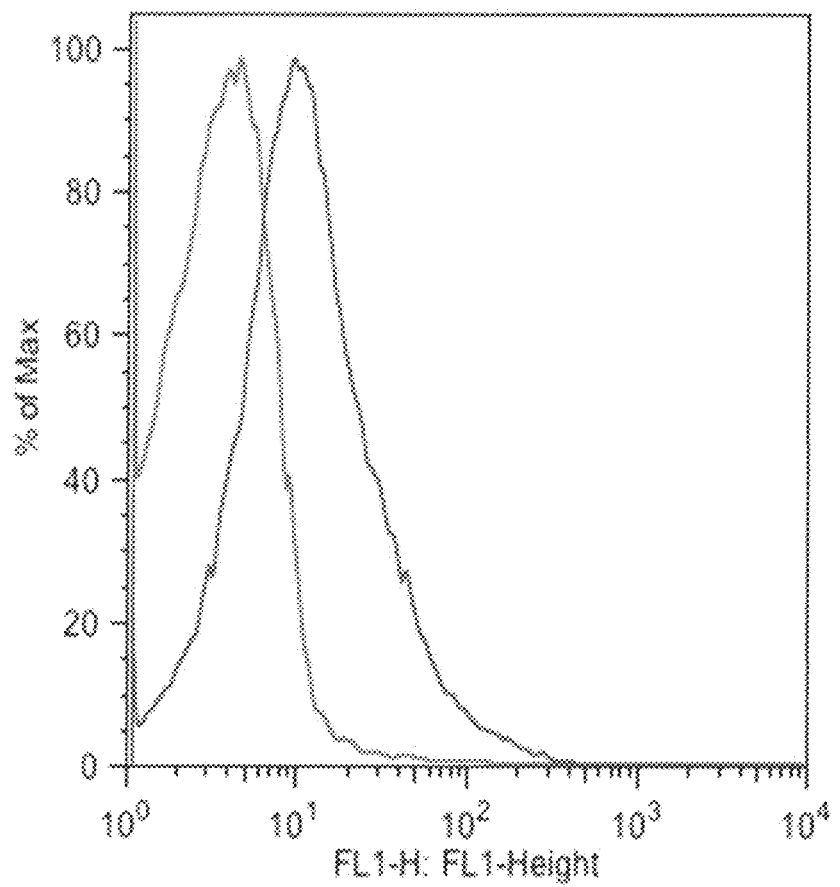
FIG. 7A, FIG. 7B and FIG. 7C. Membrane distribution of PS in normal and tumor exosomes.

Using the aliquots set aside, the exosomes obtained by ultracentrifugation of the supernatants from normal mesothelial cells and from ovarian carcinoma cells were coupled to FITC-Annexin V latex beads and subjected to FACS analyses to assess the presence of PS on the exosome surface. As predicted, the tumor-derived exosomes had PS on their surface, which is shown by the shift in the blue line (ovarian carcinoma-derived exosomes) towards the right, as compared to the red line (normal mesothelial cell-derived exosomes), towards the left in FIG. 7A.

Figure 7B:
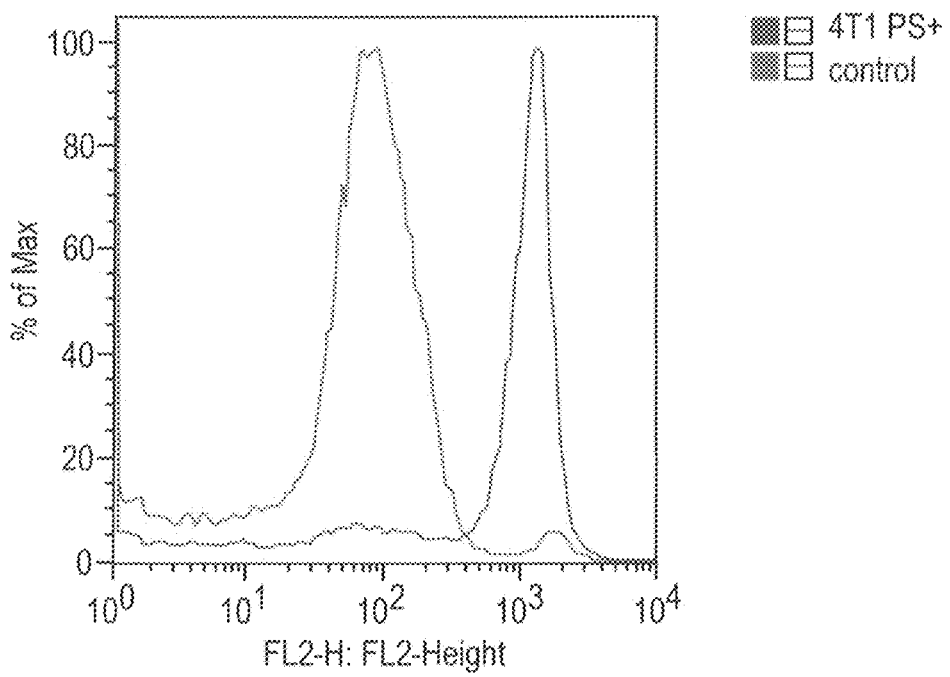
Figure 7C:
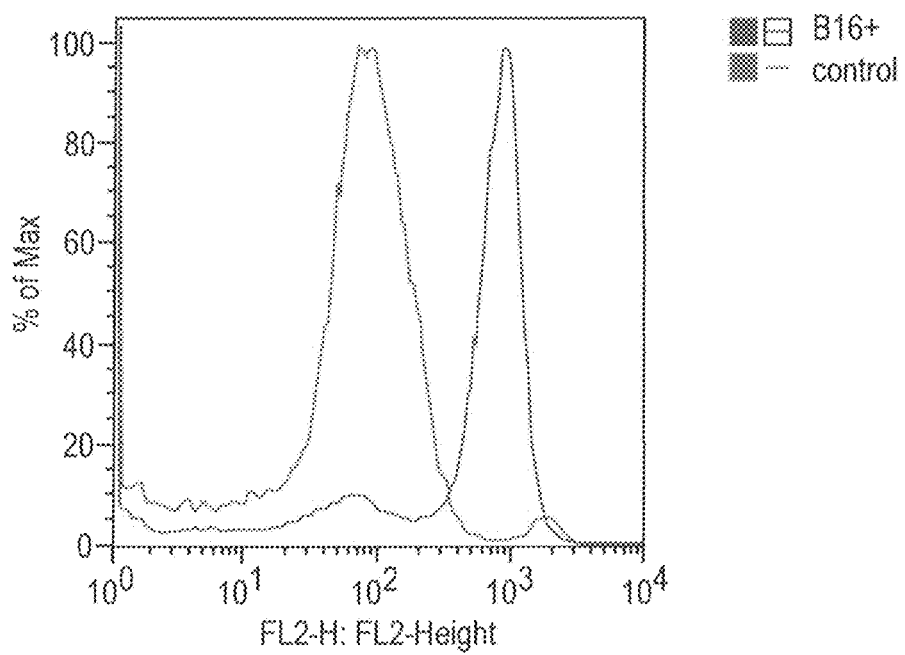

In related studies, exosomes purified from 4T1 breast carcinoma cells and B16 melanoma cells using acetate precipitation were also subjected to FACS analyses to detect surface PS. As shown in FIG. 7B and FIG. 7C, purified exosomes from both 4T1 and B16 cells, respectively, are indeed PS-positive.

The present studies therefore validate the inventors' reasoning that the acetate buffer acts via charge neutralization involving the negatively-charged PS, which is present on the surface of tumor-derived exosomes, as those exosomes reflect the PS-positive tumor cells from which they are derived. In normal cells, PS is maintained in the inner leaflet of the plasma membrane, so PS is largely absent from the surface of exosomes derived from normal cells.

Example VIII

SElective Isolation of PS-Positive Exosomes

The present example shows that the specificity of acetate buffers in precipitating PS-positive extracellular microvesicles and exosomes, such as disease-related and tumor-derived extracellular microvesicles and exosomes, applies to exosomes but not to PS-positive liposomes.

In a first study, the acetate isolation method, which has been used successfully with tumor-derived exosomes, was applied to PS-positive liposomes generated from pure phosphatidylserine and phosphatidylcholine. As shown in the previous examples, acetate buffer is effective in precipitating tumor-derived exosomes, which have PS on their surface. In contrast, applying the same methodology to an equivalent sample of liposomes having PS on their surface did not produce any visibly-detectable precipitation.

In a second study, PS-negative and PS-positive liposome populations were labeled with fluorescent lipids, permitting any amount of liposomes precipitated to be quantified. This study confirmed that acetate buffer does not precipitate any meaningful amount of phospholipid liposomes, even when PS-positive.

In this second study, two populations of fluorescent liposomes were prepared; one from phosphatidylcholine (PC) and the other from a phosphatidylcholine and phosphatidylserine mixture (PC/PS). The PC liposomes were prepared by mixing 1 mg of phosphatidylcholine with 0.1 µg of the fluorescent component, N-rhodamine-phosphatidylethanolamine (N-rho-PE) in $CHCl_3$. The solvent was evaporated and the dry lipid was rehydrated in 1.0 mL of PBS for 30 min at 20° C. The hydrated lipid mixture was vortexed and then sonicated to yield small unilamellar vesicles. The PC/PS liposomes were prepared by the same technique, except the starting material mixed 0.66 mg of PC and 0.33 mg of dioleoylphosphatidylserine (32 mol %) in $CHCl_3$ with 0.1 µg of N-rho-PE.

The separate PC and PC/PS liposome preparations were centrifuged at 5,000 g for 5 min to remove any large precipitable liposomes. The supernatants were removed and 0.4 mL from each preparation was aliquoted to two tubes. 0.5 mL of PBS was added to each tube followed by 0.1 mL of PBS or acetate buffer (1.0 M; pH 5.7), respectively. The tubes were mixed, incubated on ice for 1 hr, vortexed and 0.1 mL aliquots were removed to determine total fluorescence. Each tube was then centrifuged at 5,000 g for 5 min and 0.1 mL aliquots from the supernatant were removed to determine residual (non-precipitated) fluorescence.

Figure 8:
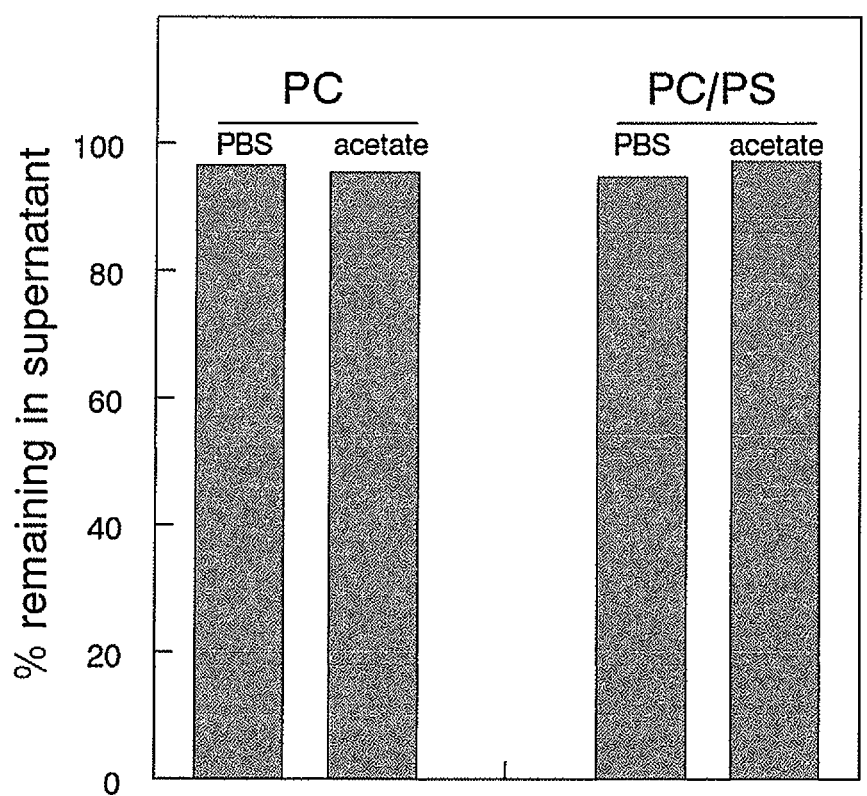
FIG. 8. Acetate buffer does not precipitate pure phospholipid liposomes. Preparations of fluorescent-labeled liposomes made from phosphatidylcholine (PC) or a PC/PS mixture (two to one ratio) were centrifuged at 5,000 g for 5 min to remove any large precipitable liposomes. The supernatants were removed and 0.4 mL from each preparation was aliquoted to two tubes. 0.5 mL of PBS was added to each tube followed by 0.1 mL of PBS or acetate buffer (1.0 M; pH 5.7), respectively. The tubes were mixed, incubated on ice for 1 hr, vortexed and 0.1 mL aliquots were removed to determine total fluorescence. Each tube was then centrifuged at 5,000 g for 5 min and 0.1 mL aliquots from the supernatant were removed to determine residual (non-precipitated) fluorescence.

The results are depicted in FIG. 8, which shows that acetate buffer does not precipitate phospholipid liposomes, even when containing substantial amounts of PS.

Together, the data of the present examples indicate that PS is required, but not sufficient, for acetate buffers to precipitate phospholipid vesicles and suggests that the specificity for isolating PS-positive microvesicles and exosomes, particularly disease-related and tumor-derived microvesicles and exosomes, stems from the interaction of the acetate buffer with the unique microvesicle/exosome composition, in which PS is expressed on the surface in association with non-lipid membrane components, particularly membrane proteins. This supports the understanding of microvesicles and exosomes as being cell-derived and/or cell-secreted microvesicles, rather than synthetic lipid vesicles.

Example IX

Separation of PS-Positive Tumor Exosomes From Mixtures

This example highlights the ability of the acetate precipitation method to selectively isolate PS-positive extracellular microvesicles such as exosomes, as exemplified by tumor-derived exosomes, from a sample containing a mixture of extracellular microvesicles and exosomes. It also shows that the specificity of acetate buffers to precipitate tumor-derived exosomes is dependent on the expression of PS on the exosomes outer membrane leaflet.

PS-positive exosomes were obtained from PS-expressing 4T1 breast carcinoma cells and PS-negative exosomes from counterpart cells. The exosomes were purified by centrifugation and confirmed to be PS-positive or PS-negative by FACS analysis with FITC-annexin (FIG. 9A).

Figure 9A:
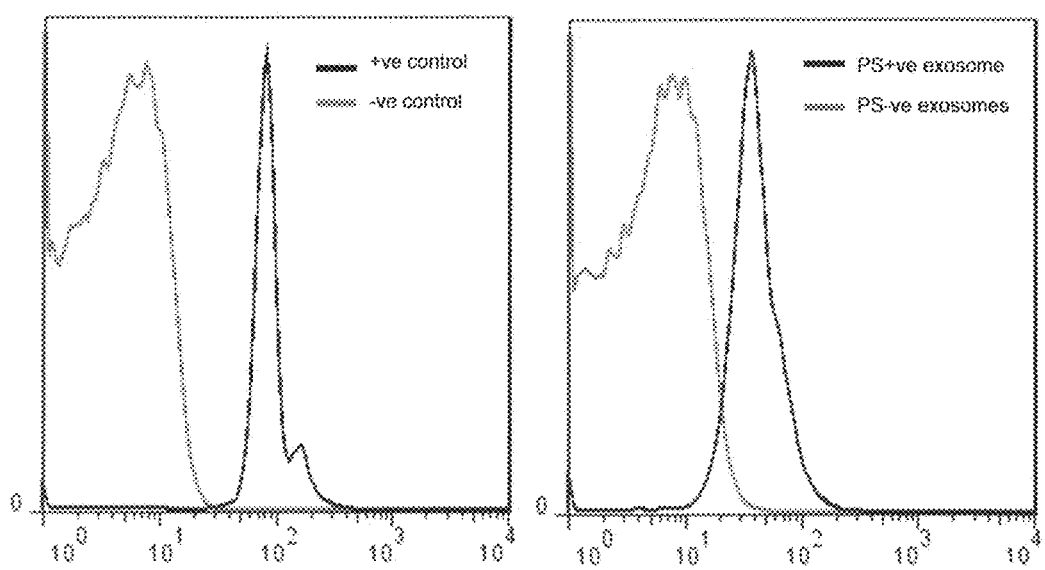
FIG. 9A and FIG. 9B. Selective isolation of PS-positive exosomes from a mixture of exosomes.

The left panel of FIG. 9A shows positive and negative controls in the form of annexin 5 covalently coupled to aldehyde-activated latex beads (positive control) and BSA-blocked latex beads (negative control). As shown in the right panel of FIG. 9A, when the different exosome populations were coupled to the latex beads and labeled with FITC-annexin 5, the PS-positive exosomes from the 4T1 breast carcinoma cells reflect the positive control of the annexin 5 beads, whereas the PS-negative exosomes mirror the profile of the BSA control, showing that they are, indeed, PS-negative.

After further ultracentrifugation, the PS-negative exosome population was labeled with N-rhodamine-phosphatidylethanolamine (N-Rho-PE, red fluorescence) and the PS-positive exosome population was labeled with N-NBD-phosphatidylethanolamine (N-NBD PE, green fluorescence). Both populations were centrifuged to remove residual unincorporated probe and samples set aside for FACS analysis.

Each exosome population separately, and a mixed population of both PS-negative and PS-positive exosomes were then incubated with $\frac{1}{10}^{th}$ volume of 1M acetate (pH 4.75) for 1 hour on ice. The suspensions were centrifuged at 2,000 g for 5 minutes, resolubilized in phosphate buffered saline and coupled to aldehyde latex beads for FACS analysis (FIG. 9B).

Figure 9B:
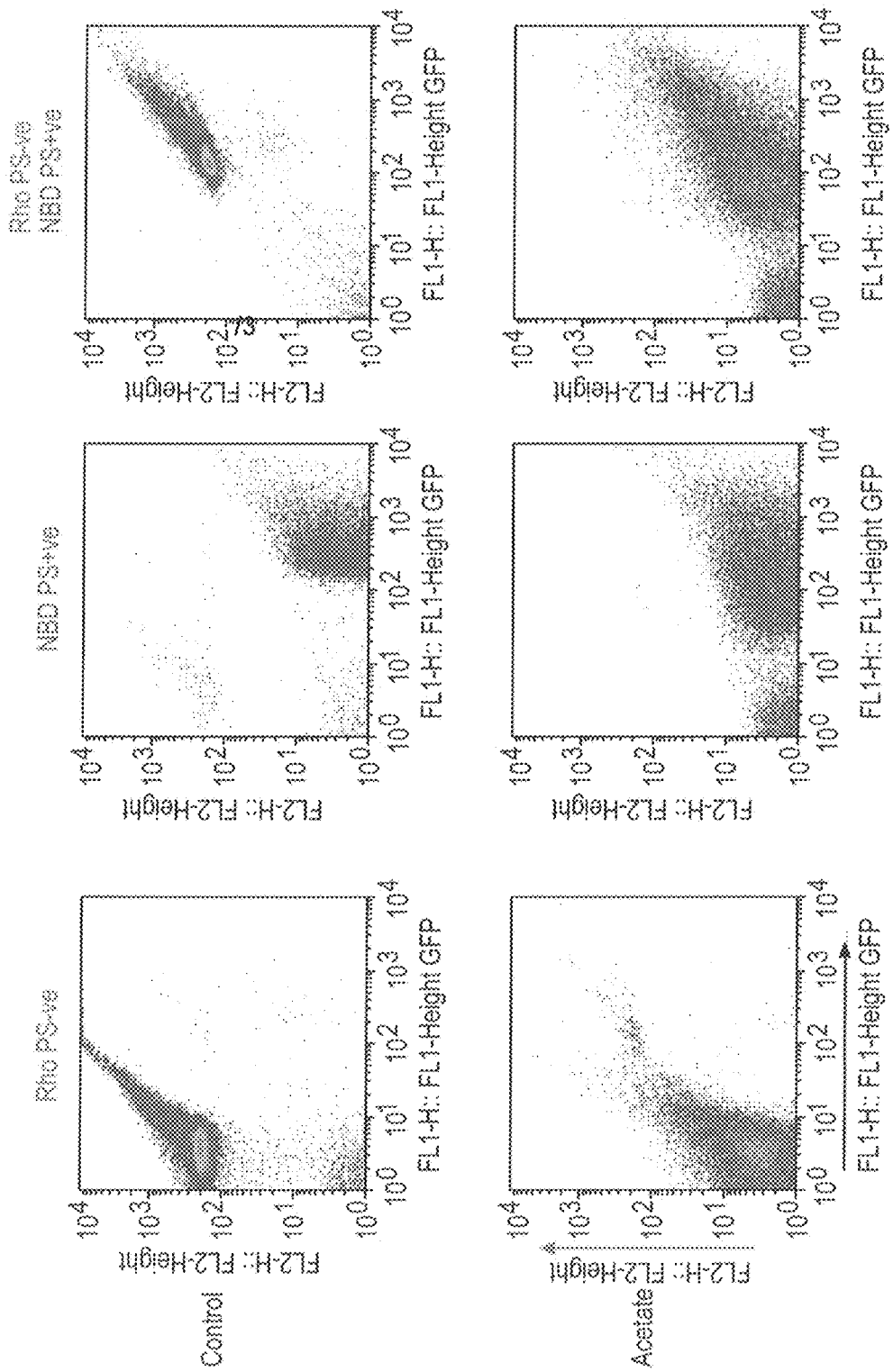

FIG. 9B shows strong fluorescent intensities of the individual and mixed populations before acetate treatment (top row). That is, the PS-negative exosomes show strong red fluorescence (top left corner of top left panel), the PS-positive exosomes show strong green fluorescence (bottom right corner of top middle panel) and the mixed population of exosomes are double-positive, with a shift in both red and green fluorescence (top right corner of top right panel). After acetate precipitation, however, only the PS-positive exosome population was recovered (FIG. 9B, bottom row). It can be seen that the red, PS-negative population was absent after precipitation, i.e., did not precipitate in acetate (no red fluorescence in the bottom left panel), whereas the green, PS-population was recovered from the acetate precipitate (strong green fluorescence in the bottom middle panel). Of great significance, only PS-positive exosomes were recovered from the mixed preparation (strong green fluorescence in the bottom right panel, without the red fluorescence seen in the corresponding top right panel).

These data therefore clearly demonstrate that acetate-mediated precipitation of tumor exosomes is dependent on the expression of PS at the exosome surface.

Example X

Phosphatidylserine Expression and Importance in Viruses

The previous examples show that the presence of phosphatidylserine (PS) is the important distinguishing factor in the use of acetate buffers to selectively isolate tumor-derived extracellular microvesicles and exosomes, as opposed to normal exosomes. The present example summarizes data from the inventors and colleagues demonstrating that PS, which is absent from the surface of normal cells, becomes exposed on virally-infected cells and viruses and has an important role in viral infections.

The methods used in demonstrating the presence of PS on the surface of virions and virally-infected cells were flow cytometry/FACS analyses, ELISA, bead depletion, immunogold labeling, PCR (including RT-PCR and Q RT-PCR) and immunofluorescence microscopy (Table 2A and Table 2B). These methods were conducted as set forth below.

In using antibodies that bind to or target PS (referred to below as "PS-targeting antibodies"), two categories of antibodies are available: those that bind to PS directly (e.g., the 9D2 antibody of Ran et al., 2002) and those that bind to PS indirectly, i.e., via a serum protein, such as $\beta_2$-glycoprotein I (e.g., the 3G4 antibody of Huang et al., 2005), where the antibodies, serum protein and PS together form a tightly-bound complex. In the following studies, all binding steps were conducted in the presence of serum (or serum proteins can also be used) to ensure effective binding of both types of PS-targeting antibodies, including the indirect binding antibodies.

A. Flow Cytometry/FACS Analysis

Permissive cells were infected with virus and at a determined time post-infection the cells were incubated with a PS-targeting antibody (primary antibody), followed by a secondary antibody to detect the primary antibody (anti-mouse or anti-human), where the secondary antibody was conjugated with a fluor, such as FITC or Texas Red. The cells were then fixed with formaldehyde and analyzed with a flow cytometer to detect fluorescent events due to binding of the primary antibody to the infected cell. Cells not infected with virus were used as a negative control to determine any background PS externalization not related to virus infection.

B. ELISA (except Ebola)

PS-targeting antibodies (primary antibodies) were coated onto polystyrene microtiter plates. The plates were then washed and blocked with either bovine serum albumin or non-heat inactivated human serum to block non-specific binding sites on the plates and then washed extensively. Dilutions of virus were added to the plates and allowed to bind at room temperature for 3 hours. The plates were then washed and viruses attached to the antibody coated plates were detected by adding biotin-conjugated virus protein-specific antibodies, washed, followed by streptavidin-horse radish peroxidase. Quantitation of peroxidase activity, which corresponds to the level of virus protein, was performed colorimetrically utilizing a spectrophotometer and compared to control standards.

C. ELISA (Ebola)

Live Ebola Zaire Virus (strain ME718; EBOV) were coated onto polystyrene microplates. Dilutions of PS-targeting antibodies (human IgG) were added to EBOV-coated plates and allowed to bind for 1-2 hours at 37° C. Bound PS-targeting antibodies were then detected by adding HRP-conjugated, goat anti-human IgG. Quantitation of peroxidase activity, which corresponds to the level of bound PS-targeting antibodies, was performed colorimetrically utilizing a spectrophotometer and compared to isotype-matched control antibody.

D. Bead Depletion

Magnetic beads coated with anti-mouse or anti-human antibodies were washed and then incubated with mouse or human PS-targeting antibodies, respectively. The coated magnetic beads were then incubated with purified virus. The magnetic beads were removed and the remaining plaque forming units in solution were determined by a standard plaque assay procedure on permissive cells.

E. Immunogold Labeling

Virions from the supernatant of infected cells were precipitated by polyethylene glycol (PEG) precipitation and isolated by ultracentrifugation on a sucrose cushion. Binding to immobilized virus by PS-targeting antibodies was determined by incubating the particles with PS-targeting antibodies conjugated to 6 nm gold particles and virus-specific antibodies conjugated to 10 nm gold particles. The sample was processed for transmission electron microscopy to visualize virus particles positive for both sized gold particles.

F. PCR, RT-PCR, Q RT-PCR

PS-targeting antibodies were coated onto polystyrene microtiter plates. The plates were then washed and bovine serum albumin and non-heat inactivated human serum were added to block non-specific binding sites on the plates and then washed extensively. Dilutions of virus were added and allowed to bind at room temperature for 3 hours. The plates were then washed and the viral nucleic acid (DNA or RNA) from viruses attached to the antibody-coated plates were isolated and purified. Viral genome quantification was performed via PCR/RT-PCR, Q RT-PCR using virus-specific sequence primers.

G. Immunofluorescence Microscopy

Cells adhering to glass coverslips were infected with virus and the binding of the PS-targeting or control antibodies to the infected cells was performed by incubating live cells with PS-targeting or control antibodies followed by removal of unbound antibody by washing with buffer. The localization of the PS-targeting and control antibodies was determined by incubation with a biotin-conjugated secondary antibody followed by incubation with FITC-conjugated streptavidin. The cells were then permeabilized with Triton X-100 and viral particles were detected with a virus-specific antibody conjugated with Alexa-594 (red). The coverslips were mounted with a nuclear stain (DAPI), and the slides were viewed by confocal microscopy for each fluorescent signal.

The above methods were used to demonstrate the presence of PS on the surface of viruses and virally-infected cells from a wide range of viral families, as set forth in Table 2A and Table 2B. In addition, data from the inventors and colleagues are presented in Table 2C and Table 2D to demonstrate that such PS exposure on viruses and virally-infected cells is not merely incidental, but has an important role in viral infections. This is shown by the use of PS-targeting antibodies to inhibit infections from diverse viral families, both in vitro and in vivo.

TABLE 2A

PS Expression and Importance Across Diverse Viral Families - Viruses

| Virus Family | Virus | Model For | Method | PS + ve |
| --- | --- | --- | --- | --- |
| Arenaviridae | Pichinde virus | Lassa Fever | Flow Cytometry ELISA | YES |
| | Junin virus Candid #1 | Hemorrhagic fever | Bead depletion ELISA Immunogold label | YES |
| Bunyaviridae | Punta Toro Virus | River Valley Fever Virus | ELISA | YES |
| Flaviviridae | Bovine viral diarrhea virus | Hepatitis C | RT-PCR | YES |
| Filoviridae | Ebola Zaire Virus (strain ME718) | Ebola | ELISA | YES |
| Herpesviridae | Varicella-zoster virus 1 | Shingles | PCR | YES |
| Orthomyxoviridae | Influenza A | Influenza | Q RT-PCR | YES |
| | Influenza B | Influenza | RT-PCR | YES |
| | Avian Influenza (H5N1) | Influenza | RT-PCR | YES |
| Paramyxoviridae | Bovine parainfluenza 3 | Influenza | RT-PCR | YES |
| | Measles | Measles | RT-PCR | YES |
| | Respiratory syncitial virus (RSV) | Pneumonia | RT-PCR | YES |
| Retroviridae | Feline immunodeficiency virus (FIV) | AIDS | RT-PCR | YES |
| | Human immunodeficiency virus 1 (HIV-1) | AIDS | ELISA | YES |
| | Human immunodeficiency virus 2 (HIV-2) | AIDS | ELISA | YES |

TABLE 2B

PS Expression and Importance Across Diverse Viral Families - Infected Cells

| Virus Family | Virus and Cells | Model For | Method | PS + ve |
| --- | --- | --- | --- | --- |
| Arenaviridae | P388D1 cells; Pichinde | Lassa Fever | FACS Analyses | YES |
| | Vero cells; Junin Virus Candid #1 | Hemorrhagic fever | Immunofluorescence Microscopy | YES |
| Bunyaviridae | RAW 264.7 cells; Punta Toro Virus | River Valley Fever Virus | FACS Analyses | YES |
| Flaviviridae | Vero cells; Yellow Fever Virus | Yellow Fever | FACS Analyses | YES |
| | Raji cells; Dengue Virus type 1 and 3 | Dengue Fever | FACS Analyses | YES |
| Filoviridae | Vero cells; Ebola Zaire Virus (strain ME718) | Ebola | FACS Analyses | YES |
| Herpesviridae | Human primary foreskin fibroblasts; human CMV | Pneumonia | FACS Analyses | YES |
| | Mouse cells infected with mouse CMV | pneumonia | FACS Analyses | YES |
| Orthomyxoviridae | U937 cells; Influenza | Influenza | FACS Analyses | YES |
| Poxviridae | U937 cells; Vaccinia | Smallpox | FACS Analyses | YES |
| Retroviridae | H9 T cells; HIV-1 | AIDS | FACS Analyses | YES |

TABLE 2C

PS Expression and Importance Across Diverse Viral Families - PS-targeting Abs In Vitro

| Virus Family | In Vitro Infection | Model For | Agent | Inhibition |
|---|---|---|---|---|
| Arenaviridae | P388D1 cells; Pichinde | Lassa Fever | PS-targeting Abs | YES |
| | Guinea pig splenocytes; Pichinde | Lassa Fever | PS-targeting Abs | YES |
| | Vero cells; Pichinde | Lassa Fever | PS-targeting Abs | YES |
| Herpesviridae | HHF-R2 cells; human CMV | Pneumonia | PS-targeting Abs | YES |
| Paramyxoviridae | A549 cells; respectively | Pneumonia | PS-targeting Abs | YES |
| Retroviridae | PBMCs; HIV-1 | AIDS | PS-targeting Abs | YES |
| Rhabdoviridae | HHF-R2 cells; vesicular stomatitis virus (VSV) | Respiratory Disease | PS-targeting Abs | YES |

TABLE 2D

PS Expression and Importance Across Diverse Viral Families: PS-targeting Abs In Vivo

| Virus Family | In Vivo Infection | Model/Disease | Inhibition and Comments |
|---|---|---|---|
| Arenaviridae | Guinea pigs; lethal dose of Pichinde | Lassa Fever | YES; 50% survival vs. 0% control |
| | Guinea pigs; lethal Pichinde, after symptoms develop | Lassa Fever | YES 50% survival vs. 0% control |
| | Surviving guinea pigs re-challenged with lethal Pichinde | Lassa Fever | YES 100% survival |
| | Guinea pigs; lethal Pichinde, combo with ribavirin | Lassa Fever | YES Additive anti-viral effect |
| | Hamsters - Pichinde | Lassa Fever | YES 30% survival vs. 5% control |
| Flaviviridae | Human Patients; Hepatitis C virus (HCV) | Hepatitis C | YES Dose-dependent reduced viral load |
| Herpesviridae | BALB/c mice; LD$_{80}$ mCMV | Pneumonia | YES 100% survival vs. 21% control |
| | SCID mice; LD$_{80}$ mCMV | Pneumonia | YES 67% survival vs. 17% control |
| | Rabbits; ocular HSV-1 | Herpetic keratitis | YES Equal or better than standard of care (ganciclovir) |
| Orthomyxoviridae | Ferrets; low pathogenic influenza | Influenza | YES Reduced lung pathology |
| Rhabdoviridae | Mice; non-lethal VSV | Respiratory Disease | YES Significantly lower viral titers |

Example XI

Isolating Viral Microvesicles Using Acetate Buffers

The present example shows that methods for isolating extracellular microvesicles such as exosomes using acetate buffers are also effective in precipitating extracellular microvesicles such as exosomes from virally-infected cells and viral cultures.

About $2.5\times10^8$ Vero cells were cultured in virus infection media (DMEM, 2% fetal bovine serum with antibiotic and antimycotic) and evenly divided into three populations (a total of 1,000 ml media for each population, dispersed into about 25 T225 flasks for each population). After about 2 doublings in 2 days, a first cell population was mock-infected as a negative control; a second cell population was infected with simian vacuolating virus 40 (SV40) Strain Pa-57, LN L1412A, at 0.1 multiplicity of infection (MOI); and a third cell population was infected with herpes simplex virus-1 (HSV-1) Strain F, LN H1411B, at 0.05 MOI. SV40 is a non-enveloped virus of the Polyomaviridae family and HSV-1 is an enveloped virus of the Herpesviridae family.

The mock, SV40 and HSV-1 infections were harvested at days 4, 7, and 3 post-infection, respectively. Cells and cell debris were first removed by low speed centrifugation (1,000 g for 30 min) and large particles were removed from those supernatants by further centrifugation at 12,000 g for 30 min. Aliquots of the supernatants from each of the infections were set aside for quantifying infectious virus.

Each of the cleared supernatants from the mock, SV40 and HSV-1 infections were separately mixed with $1/10^{th}$ volume of sodium acetate (1.0 M; pH 4.75), left on ice for 60 min and then centrifuged at 12,000 g for 30 min. The mock, SV40 and HSV-1 supernatants were each retained separately and neutralized with 1M NaOH. Any acetate-precipitated pellets from the mock, SV40 and HSV-1 infections were separately resuspended in a final volume of about 2 ml of resuspension buffer (10 mM Tris, pH 7.5, 115 mM NaCl, 1 mM EGTA), taking care that the acidity was fully neutralized (including by an additional suspension and centrifugation step, if necessary). Aliquots of the supernatants and resuspended pellets from these acetate precipitations were set aside for quantifying infectious virus.

The visual results from the acetate precipitation applied to the mock, SV40 and HSV-1 infections are shown in FIG. 10A, FIG. 10B and FIG. 10C, respectively. As can be seen, whilst there is almost no pellet visible from the mock infection (FIG. 10A), the acetate precipitation protocol produced sizeable, visible pellets from both the SV40 (FIG. 10B) and HSV-1 (FIG. 10C) infections.

Example XII

Isolated Viral Microvesicles are Largely Virus-Free

This example shows that extracellular microvesicles such as exosomes obtained by acetate precipitation from virally-infected cells and viral cultures are essentially free from infectious virus.

In the study of the previous example, the amounts of infectious SV40 and HSV-1 virus prior to acetate precipitation, and the amounts of infectious virus remaining in the supernatants and pellets following acetate precipitation, were quantified using a $TCID_{50}$ assay, which tests for infectivity. $TCID_{50}$ is a measure of infectious virus titer. This endpoint dilution assay quantifies the amount of virus required to produce a cytopathic effect in 50% of inoculated tissue culture cells (in this case, Vero cells). The theoretical relationship between $TCID_{50}$ and plaque-forming unit (PFU) is that 1 $TCID_{50}$ equals 0.69 PFU. The results are set forth in Table 3.

TABLE 3

Substantial Removal of Infectious Virus Using Acetate Precipitation

| Sample | IU/ml, $TCID_{50}$ | Volume (ml) | Total IU, $TCID_{50}$ |
|---|---|---|---|
| SV40 before acetate | $5.8 \times 10^8$ | 1,000 | $5.8 \times 10^{11}$ |
| SV40 acetate supernatant | $2 \times 10^6$ | 1,000 | $2 \times 10^9$ |
| SV40 acetate pellet | $1 \times 10^8$ | 1.5 | $1.5 \times 10^8$ |
| HSV-1 before acetate | $5 \times 10^7$ | 1,000 | $5 \times 10^{10}$ |
| HSV-1 acetate supernatant | $1 \times 10^6$ | 1,000 | $1 \times 10^9$ |
| HSV-1 acetate pellet | $3.16 \times 10^7$ | 2.0 | $6.32 \times 10^7$ |

As shown in Table 3, it can be seen that 1,000 ml of SV40-containing media had a total of $5.8 \times 10^{11}$ IU virus. After subjecting to acetate precipitation, the amount of virus in the supernatant and pellet combined was $2.15 \times 10^9$, indicating that $5.7785 \times 10^{11}$ IU of SV40 virus had been removed and/or inactivated during the procedure. Thus, 99.63% of infectious SV40 virus was removed and/or inactivated during acetate precipitation. Of the 0.37% infectious SV40 virus remaining after acetate precipitation, 92.5% is in the supernatant, such that, of the original starting material, only 0.028% infectious SV40 virus was present in the pellet.

Similarly, as shown in Table 3 for HSV-1, 1,000 ml of HSV-1-containing media had a total of $5.8 \times 10^{10}$ IU virus. After subjecting to acetate precipitation, the amount of virus in the supernatant and pellet combined was $1.063 \times 10^9$, indicating that $5.694 \times 10^{10}$ IU of HSV-1 virus had been removed and/or inactivated during the procedure. In this case, 98.17% of infectious HSV-1 virus was removed and/or inactivated during acetate precipitation. Of the 1.83% infectious HSV-1 virus remaining after acetate precipitation, 93.7% is in the supernatant, such that, of the original starting material, only 0.11% infectious HSV-1 virus is present in the pellet.

With the objective being to prepare viral-derived exosomes and/or microvesicles via the acetate precipitation method, it is therefore advantageous that the sizeable pellets observed in FIG. 10B and FIG. 10C are both essentially free from infectious virus.

Example XIII

Further Characterization of Isolated Viral Microvesicles

The present example reports the results of preliminary characterization of the viral-derived extracellular microvesicles and exosomes isolated using the acetate precipitation.

A. Gradient Purification

Although using different terminology, Szilagyi and Cunningham (1991) reported the presence of non-infectious, HSV-1 membrane-enclosed particles that would now be termed viral-derived exosomes or microvesicles. Using a 5-15% Ficoll® gradient purification of HSV-1, they observed two bands of particles: a sharp lower band and a more diffuse upper band (see FIG. 1 in Szilagyi and Cunningham, 1991). The lower band (termed Heavy or H particles) was reported to contain almost exclusively HSV-1 virions, whereas the upper band was said to contain mainly non-infectious, membrane-enclosed particles (termed Light or L particles), albeit cross-contaminated with 0.1 to 0.5% infectious H particles (see Table 1 in Szilagyi and Cunningham, 1991). The L particles were reported to resemble the virions in appearance, but lacked the viral nucleocapsid and were not infectious. It is these "L particles" that would now be termed viral-derived microvesicles or exosomes.

Generally following the Szilagyi and Cunningham (1991) technique, a sample of the resuspended pellet from the acetate precipitations of the HSV-1 infection was applied to a 5-15% Ficoll® gradient. The resuspended pellet material was layered onto 35 ml preformed gradient of 5-15% Ficoll® 400 suspended in modified medium and centrifuged at 26,000 g for 2 hours at 4° C. The presence of one band on top of the 5% Ficoll fraction (F5) was observed, along with one band on top of the 15% fraction (F15), both visible by eye. These are similar to the light (F5) and heavy (F15) bands reported by Szilagyi and Cunningham (1991), except the F15 band in the present study was more diffuse.

The materials in the two bands were removed separately by puncturing the side of the tube with a needle on a syringe. Aliquots were taken for quantifying infectious virus using the same $TCID_{50}$ assay described above. Of the infectious virus loaded onto the Ficoll® gradient, only about 0.2% was recovered from the light, F5 fraction.

B. FACS Analyses

Samples of the resuspended pellets from the acetate precipitation of the mock and SV40 infections, and the two fractions (F5 and F15) from the Ficoll® separation of the HSV-1 acetate precipitation were then subjected to FACS analyses. The different fractions (15 μg protein each) were bound to latex beads and analyzed by FACS using the following detection agents.

For SV40 viral antigen, a rabbit polyclonal antibody to SV40 VP1, a major capsid protein, was used; and for HSV-1 viral antigen, a mouse monoclonal antibody to HSV gB, a surface glycoprotein known to be present in both virions (H) and so-called L particles, was used. Anti-rabbit and anti-mouse antibodies conjugated to the fluorescent probe allophycocyanin (APC) were used to detect the SV40 and HSV-1 antibodies, respectively. An anti-CD63 antibody conjugated to phycoerythrin (PE) was used to detect microvesicles or exosomes, as CD63 is a membrane-associated protein present in exosomes. Annexin V conjugated to FITC was used to detect PS. Negative controls included BSA-latex beads and isotype control antibodies conjugated to PE or APC.

Figure 11A:
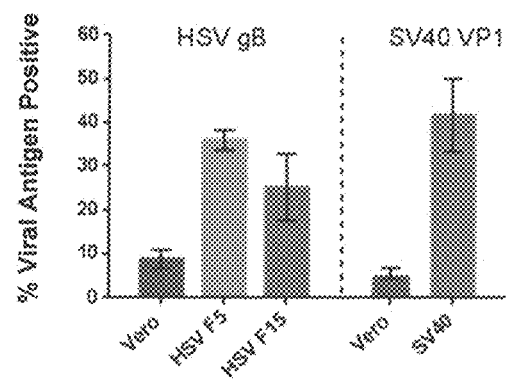
FIG. 11A, FIG. 11B and FIG. 11C.
Figure 11B:
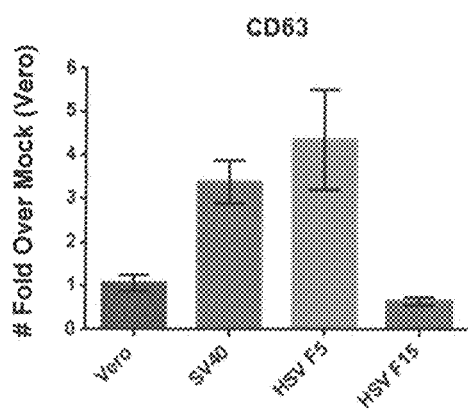
Figure 11C:
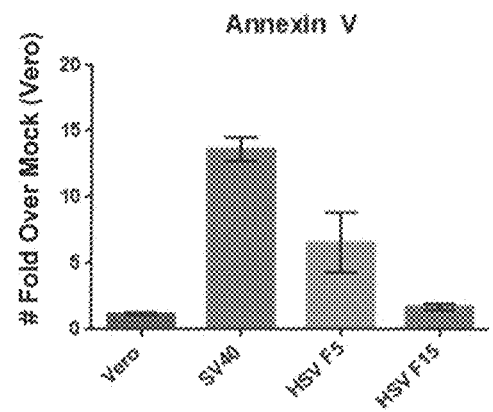

Comparative results from the FACS analyses of the acetate pellets from the mock infection (labelled Vero), the SV40 infection and the F5 and F15 fractions from the HSV-1 infection are shown in FIG. 11A, FIG. 11B and FIG. 11C. From FIG. 11A, it can be seen that the acetate precipitated samples remain positive for their respective viral antigens (HSV gB and SV40 VP1). In comparison to the background determined from the mock infection, each of the SV40 and HSV-1 acetate precipitates are also positive for the exosome marker, CD63 (FIG. 11B) and PS, as shown for the Annexin V binding (FIG. 11C). For the HSV-1 resuspended acetate pellets, which were further fractionated into heavy (F15) and light (F5) bands, both CD63 and PS were identified in the F5 fraction, which matches the L particles reported in the literature (Szilagyi and Cunningham, 1991).

Together, these data are therefore consistent with the isolation of essentially non-infectious, PS-positive, extracellular microvesicles and exosomes from cells infected with both enveloped and non-enveloped viruses.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aharon and Brenner, "Microparticles, thrombosis and cancer", *Best Practice & Research Clinical Haematology*, 22:61-69, 2009.

Al Nedawi et al., "Mast cell-derived exosomes activate endothelial cells to secrete plasminogen activator inhibitor type 1", *Arterioscler. Thromb. Vasc. Biol.*, 25:1744-1749, 2005.

Andre et al., "Exosomes as potent cell-free peptide-based vaccine. I. Dendritic cell-derived exosomes transfer functional MHC class I/peptide complexes to dendritic cells", *J. Immunol.*, 172:2126-2136, 2004.

Andreola et al., "Induction of lymphocyte apoptosis by tumor cell secretion of FasL-bearing microvesicles", *J. Exp. Med.*, 195:1303-1316, 2002.

Best, "Viruses play dead to TAMe interferon responses", *Cell Host & Microbe*, 14(2):117-8, 2013.

Bhattacharyya et al., "Enveloped viruses disable innate immune responses in dendritic cells by direct activation of TAM receptors", *Cell Host & Microbe*, 14(2):136-147, 2013.

Bizik et al., "Human tumor cells synthesize and secrete alpha-2-macroglobulin in vitro", *Int. J. Cancer*, 37:81-88, 1986.

Chaput et al., "The potential of exosomes in immunotherapy", *Expert. Opin. Biol. Ther.*, 5:737-747, 2005.

Chen et al., "Phosphatidylserine Vesicles Enable Efficient En Bloc Transmission of Enteroviruses", *Cell*, 160:619-630, 2015.

Cho et al., "MHC independent anti-tumor immune responses induced by Hsp70-enriched exosomes generate tumor regression in murine models", *Cancer Lett.*, 275:256-265, 2009. Clayson, et al., "Release of Simian Virus 40 Virions from Epithelial Cells is Polarized and Occurs without Cell Lysis", *J. Virology*, 63(5):2278-2288, 1989.

Clayton et al., "Analysis of antigen presenting cell derived exosomes, based on immuno-magnetic isolation and flow cytometry", *J. Immunol. Methods*, 247:163-174, 2001.

Connor et al., "The majority of circulating platelet-derived microparticles fail to bind annexin V, lack phospholipid-dependent procoagulant activity and demonstrate greater expression of glycoprotein Ib", *Thromb. Haemost.*, 103(5):1044-1052, 2010.

Czuczman et al., "*Listeria monocytogenes* exploits efferocytosis to promote cell-to-cell spread", *Nature*, 509:230-234, 2014.

Dai et al., "Phase I clinical trial of autologous ascites-derived exosomes combined with GM-CSF for colorectal cancer", *Mol. Ther.*, 16:782-790, 2008.

DaMatta et al., "*Trypanosoma cruzi* exposes phosphatidylserine as an evasion mechanism", *FEMS Microbiol. Lett.*, 266:29-33, 2007.

Dawson et al., "Data for Biochemical Research", 3rd Ed., Oxford Science, 1986.

Eda & Sherman, "Cytoadherence of Malaria-Infected Red Blood Cells Involves Exposure of Phosphatidylserine", *Cell Physiol. Biochem.*, 12:373-384, 2002.

Escudier et al., "Vaccination of metastatic melanoma patients with autologous dendritic cell (DC) derived-exosomes: results of the first phase I clinical trial", *J. Transl. Med.*, 3:10, 2005.

Flint et al., *Princilpes of Virology: Molecular Biology, Pathogenesis, and Control*, Washington, D.C. ASM Press, 2000.

Francis et al., "*Mycobacterium tuberculosis* ESAT-6 is a leukocidin causing Ca2+ influx, necrosis and neutrophil extracellular trap formation", *Cell Death and Disease*, 5:e1474; doi:10.1038/cddis.2014.394, 2014.

Goth & Stephens, "Rapid, Transient Phosphatidylserine Externalization Induced in Host Cells by Infection with *Chlamydia* spp", *Infect. Immun.*, 69(2):1109-1119, 2001.

Grant et al., "A filtration-based protocol to isolate human Plasma Membrane-derived Vesicles and exosomes from blood plasma", *J. Immunol. Methods*, 371(1-2):143-51, 2011.

György et al., "Membrane vesicles, current state-of-the-art: emerging role of extracellular vesicles", *Cell. Mol. Life Sci.*, 68:2667-2688, 2011.

Hägele et al., "*Legionella pneumophila* kills human phagocytes but not protozoan host cells by inducing apoptotic cell death", *FEMS Microbiol. Lett.*, 169(1):51-58, 1998.

Huang, Bennett, Thorpe, "A monoclonal antibody that binds anionic phospholipids on tumor blood vessels enhances the antitumor effect of docetaxel on human breast tumors in mice," *Cancer Res.*, 65:4408-4416, 2005.

Huber et al., "Human colorectal cancer cells induce T-cell death through release of proapoptotic microvesicles: role in immune escape", *Gastroenterology*, 128:1796-1804, 2005.

Iero et al., "Tumour-released exosomes and their implications in cancer immunity", *Cell Death. Differ.*, 15:80-88, 2008.

Izquierdo-Useros et al., "HIV and mature dendritic cells: Trojan exosomes riding the Trojan horse?", *PLoS Pathog*, 6(3):e1000740, 2010.

Jemielity et al., "TIM-Family Proteins Promote Infection of Multiple Enveloped Viruses through Virion-Associated Phosphatidylserine", *PLoS Pathogens*, 9(3):e1003232; 2013.

Keller et al., "Systemic presence and tumor-growth promoting effect of ovarian carcinoma released exosomes", *Cancer Lett.*, 278:73-81, 2009.

Kennedy et al., "Attenuating a sickle cell crisis with annexin V", *Medical Hypotheses*, http://dx.doi.org/10.1016/j.mehy.2015.01.037, 2015.

Kim et al., "Fas ligand-positive membranous vesicles isolated from sera of patients with oral cancer induce apoptosis of activated T lymphocytes", *Clin. Cancer Res.*, 11:1010-1020, 2005.

Koga et al., "Purification, characterization and biological significance of tumor-derived exosomes", *Anticancer Res.*, 25:3703-3708, 2005.

Logozzi et al., "High levels of exosomes expressing CD63 and caveolin-1 in plasma of melanoma patients", *PLoS One*, 4:e5219, 2009.

Lonsdale et al., "Phosphatidylserine as a Therapeutic Target for the treatment of *Francisella tularensis* and *Yersinia pestis* infections", Chemical & Biological Defense Science & Technology Conference, 2011 Las Vegas, Nev. Abstract W15-048.

Mallat et al., "Shed Membrane Microparticles With Procoagulant Potential in Human Atherosclerotic Plaques", *Circulation,* 99:348-353, 1999.

Marx et al., "Heat denaturation of fibrinogen to develop a biomedical matrix", *J. Biomed. Mater. Res. B AppL Biomater.,* 84:49-57, 2008.

Meckes et al., "Human tumor virus utilizes exosomes for intercellular communication", *Proc. Natl. Acad. Sci. USA,* 107(47):20370-20375, 2010.

Meckes and Raab-Traub, "Microvesicles and Viral Infection", *J. Virology,* 85(24):12844-12854, 2011.

Meertens et al., "The TIM and TAM families of phosphatidylserine receptors mediate dengue virus entry", *Cell Host & Microbe,* 12(4):544-557, 2012.

Mercer and Helenius, "Vaccinia virus uses macropinocytosis and apoptotic mimicry to enter host cells", *Science,* 320:531-535, 2008.

Millar et al., "An evaluation of the heat precipitation method for plasma fibrinogen estimation", *J. Clin. Pathol.,* 24:827-830, 1971.

Mitchell et al., "Increased exosome production from tumour cell cultures using the Integra CELLine Culture System", *J. Immunol. Methods,* 335:98-105, 2008.

Moller-Tank & Maury, "Phosphatidylserine receptors: Enhancers of enveloped virus entry and infection", Virology, http://dx.doi.org/10.1016/j.virol.2014.09.009; 468-470 (2014) 565-580, 2014.

Moody et al., "Anti-phospholipid human monoclonal antibodies inhibit CCR5-tropic HIV-1 and induce β-chemokines", *J. Exp Med.,* 207(4):763-776, 2010.

Morgan Jr, "alpha 2-macroglobulin production by cultured human melanoma cells", *J. Natl. Cancer Inst.,* 72:557-562, 1984.

Morizono et al., "The soluble serum protein Gas6 bridges virion envelope phosphatidylserine C254 to the TAM receptor tyrosine kinase Ax1 to mediate viral entry", *Cell Host Microbe,* 9:286-298. 2011.

Murata-Kamiya et al., "*Helicobacter pylori* Exploits Host Membrane Phosphatidylserine for Delivery, Localization, and Pathophysiological Action of the CagA Oncoprotein", *Cell Host Microbe,* 7:399-411, 2010.

Parolini et al., "Microenvironmental pH is a key factor for exosome traffic in tumor cells"' *J. Biol. Chem.,* 284: 34211-34222, 2009.

Pattanapanyasat et al., "Febrile temperature but not proinflammatory cytokines promotes phosphatidylserine expression on *Plasmodium falciparum* malaria-infected red blood cells during parasite maturation", *Cytometry, Part A,* 77A:515-523, 2010.

Petersen & Krogfelt, "*Helicobacter pylori*: an invading microorganism? A review", *FEMS Immunol. Med. Microbiol.,* 36:117-126, 2003.

Rabinowits et al., "Exosomal microRNA: a diagnostic marker for lung cancer"' *Clin. Lung Cancer,* 10:42-46, 2009.

Ran, Downes, Thorpe, "Increased exposure of anionic phospholipids on the surface of tumor blood vessels," *Cancer Res.,* 62 6132-6140, 2002.

Sabatier et al., "Type 1 And Type 2 Diabetic Patients Display Different Patterns of Cellular Microparticles", *Diabetes,* 51:2840-2845, 2002.

Schorey & Bhatnagar, "Exosome Function: From Tumor Immunology to Pathogen Biology", *Traffic,* 9:871-881, 2008.

Schubert-Unkmeir et al., "Gene Expression Pattern in Human Brain Endothelial Cells in Response to *Neisseria meningitidis", Infect. Immun.,* 75(2):899-914, 2007.

Seabra et al., "*Toxoplasma gondii* exposes phosphatidylserine inducing a TGF-beta1 autocrine effect orchestrating macrophage evasion", *Biochem. Biophys. Res. Comm.,* 324(2):744-752, 2004.

Simons & Raposo, "Exosomes—vesicular carriers for intercellular communication", *Current Opinion in Cell Biology,* 21:575-581, 2009.

Simpson and Mathivanan, "Extracellular Microvesicles: The Need for Internationally Recognised Nomenclature and Stringent Purification Criteria", *J. Proteomics Bioinform.,* 5:2 http://dx.doi.org/10.4172/jpb.10000e10, 2012.

Sims et al., "Neural stem cell-derived exosomes mediate viral entry", Int. J. Nanomedicine, 9:4893-4897, 2014.

Skog et al., "Glioblastoma microvesicles transport RNA and proteins that promote tumour growth and provide diagnostic biomarkers" *Nat. Cell Biol.,* 10:1470-1476, 2008.

Soares et al., "Targeting inside-out phosphatidylserine as a therapeutic strategy for viral diseases", *Nature Medicine,* 14(12):1357-1362, 2008.

Souza et al., "Microparticles: markers and mediators of sepsis-induced microvascular dysfunction, immunosuppression, and AKI", *Kidney Int., doi:* 10.1038/ki.2015.26, 2015.

Szajnik et al., "Tumor-derived microvesicles induce, expand and up-regulate biological activities of human regulatory T cells (Treg)", *PLoS One,* 5:e11469, 2010.

Szilagyi and Cunningham, "Identification and characterization of a novel non-infectious herpes simplex virus-related particle", *J. Gen. Virol.,* 72:661-668, 1991.

Taylor and Gercel-Taylor, "MicroRNA signatures of tumor-derived exosomes as diagnostic biomarkers of ovarian cancer", *Gynecol. Oncol.,* 110:13-21, 2008.

Taylor et al., "Exosome isolation for proteomic analyses and RNA profiling", *Methods Mol. Biol.,* 728:235-246, 2011.

Thery et al., "Exosomes: composition, biogenesis and function", *Nat. Rev. Immunol.,* 2:569-579, 2002.

Thery et al., "Isolation and characterization of exosomes from cell culture supernatants and biological fluids", *Curr. Protoc. Cell Biol.*, Chapter 3:Unit, 2006.

Thery et al., "Membrane vesicles as conveyors of immune responses", *Nat. Rev. Immunol.*, 9:581-593, 2009.

U.S. Patent Application Publication No. 2013/0052647 A1

U.S. Patent Application Publication No. 2013/0337440 A1

U.S. Pat. No. 7,262,167

U.S. Pat. No. 7,790,159

U.S. Pat. No. 7,906,115;

U.S. Pat. No. 8,288,172

U.S. Pat. No. 8,530,228

U.S. Pat. No. 8,901,284 van der Kleij et al., "A Novel Host-Parasite Lipid Cross-talk: schistosomal lyso-phosphatidylserine activates toll-like receptor 2 and affects immune polarization", *J. Biol. Chem.*, 277(50):48122-48129, 2002.

Valenti et al., "Tumor-released microvesicles as vehicles of immunosuppression", *Cancer Res.*, 67:2912-2915, 2007.

Walker et al., "Cytomegalovirus-infected human endothelial cells can stimulate allogeneic CD4+ memory T cells by releasing antigenic exosomes'" *J. Immunol.*, 182(3): 1548-1559, 2009.

Wanderley et al., "Cooperation between apoptotic and viable metacyclics enhances the pathogenesis of leishmaniasis", *PLoS One*, 4(5):e5733, 2009.

Wanderley et al., "Phosphatidylserine exposure on the surface of *Leishmania amazonensis* amastigotes modulates in vivo infection and dendritic cell function", *Parasite Immunology*, 35:109-119, 2013.

Wandler et al., "A Greasy Foothold for *Helicobacter pylori*", *Cell Host Microbe*, 7:338-339, 2010.

Wieckowski et al., "Tumor-derived microvesicles promote regulatory T cell expansion and induce apoptosis in tumor-reactive activated CD8+ T lymphocytes", *J. Immunol.*, 183:3720-3730, 2009.

Wu et al., "Derivation of androgen-independent human LNCaP prostatic cancer cell sublines: Role of bone stromal cells", *Int. J. Cancer*, 57(3):406-412, 1994.

Yuyama et al., "Sphingolipid-modulated Exosome Secretion Promotes Clearance of Amyloid-β by Microglia", *J. Biol. Chem.*, 287(14):10977-10989, 2012.

Zandbergen et al., "*Leishmania* disease development depends on the presence of apoptotic promastigotes in the virulent inoculum", *Proc. Natl. Acad. Sci. USA.*, 103(37): 13837-13842, 2006.

Zwaal and van Deenen, "Interactions between proteins and lipids from human red cell membranes", *Chem. Phys. Lipids*, 4:311-322, 1970.

What is claimed is:

1. A method of isolating phosphatidylserine-positive extracellular microvesicles from a biological fluid, wherein said phosphatidylserine-positive extracellular microvesicles have negatively-charged phosphatidylserine on their surface; said method comprising precipitating phosphatidylserine-positive extracellular microvesicles from said biological fluid, wherein said precipitating comprises contacting a sample of said biological fluid with an acetate buffer at a pH and concentration effective to precipitate phosphatidylserine-positive extracellular microvesicles from said biological fluid; and collecting said phosphatidylserine-positive extracellular microvesicles from the precipitate, thereby isolating said phosphatidylserine-positive extracellular microvesicles.

2. The method of claim 1, wherein said phosphatidylserine-positive extracellular microvesicles are viral-derived extracellular microvesicles from a virally-infected cell.

3. The method of claim 1, wherein said phosphatidylserine-positive extracellular microvesicles are tumor-derived extracellular microvesicles.

4. The method of claim 1, wherein said acetate buffer has a pH of between about 4.25 and about 5.25.

5. The method of claim 1, wherein said acetate buffer has a final concentration in said sample of between about 0.05M and about 0.25M.

6. The method of claim 1, wherein said biological fluid is a human biological fluid.

7. A method of isolating viral-derived extracellular microvesicles from a virally-infected cell, wherein said viral-derived extracellular microvesicles are phosphatidylserine-positive extracellular microvesicles that have negatively-charged phosphatidylserine on their surface; said method comprising precipitating viral-derived extracellular microvesicles from a biological fluid, wherein said precipitating comprises contacting a sample of biological fluid that contains viral-derived extracellular microvesicles with an acetate buffer at a pH and concentration effective to precipitate viral-derived extracellular microvesicles from said biological fluid; and collecting the viral-derived extracellular microvesicles from the precipitate, thereby isolating viral-derived extracellular microvesicles.

8. The method of claim 7, wherein said method isolates viral-derived extracellular microvesicles substantially free from infectious virus.

9. The method of claim 7, wherein said viral-derived extracellular microvesicles are viral-derived exosomes.

10. The method of claim 7, wherein said acetate buffer has a pH of between about 4.25 and about 5.25.

11. The method of claim 7, wherein said acetate buffer has a final concentration in said sample of between about 0.05M and about 0.25M.

12. The method of claim 7, wherein said acetate buffer is essentially free from volume excluding polymers.

13. The method of claim 7, wherein said biological fluid is a human biological fluid.

14. A method of isolating tumor-derived extracellular microvesicles from a biological fluid, wherein said tumor-derived extracellular microvesicles are phosphatidylserine-positive extracellular microvesicles that have negatively-charged phosphatidylserine on their surface; said method comprising precipitating tumor-derived extracellular microvesicles from said biological fluid, wherein said precipitating comprises contacting a sample of said biological fluid with an acetate buffer at a pH and concentration effective to precipitate tumor-derived extracellular microvesicles from said biological fluid; and collecting said tumor-derived extracellular microvesicles from the precipitate, thereby isolating said tumor-derived extracellular microvesicles.

15. The method of claim 14, wherein said tumor-derived extracellular microvesicles are tumor-derived exosomes.

16. The method of claim 15, wherein said biological fluid contains a mixed population of exosomes comprising tumor-derived and normal exosomes, and wherein said method selectively precipitates said tumor-derived exosomes from said mixed population, as opposed to said normal exosomes.

17. The method of claim 15, wherein said tumor-derived exosomes are exosomes from melanoma, colorectal cancer, lung cancer, pancreatic cancer, liver cancer, prostate cancer, breast cancer or ovarian cancer.

18. The method of claim 15, wherein said tumor-derived exosomes are human tumor exosomes.

19. The method of claim 15, wherein said tumor-derived exosomes are isolated without substantially damaging their morphological or functional properties or cell surface antigens.

20. The method of claim 14, wherein said acetate buffer has a pH of between about 4.25 and about 5.25.

21. The method of claim 20, wherein said acetate buffer has a pH of between about 4.5 and about 5.0.

22. The method of claim 21, wherein said acetate buffer has a pH of about 4.75.

23. The method of claim 14, wherein said acetate buffer has a final concentration in said sample of between about 0.05M and about 0.25M.

24. The method of claim 23, wherein said acetate buffer has a final concentration in said sample of between about 0.05M and about 0.1M.

25. The method of claim 23, wherein 1/10th volume of 1.0M acetate buffer is added to said sample.

26. The method of claim 14, wherein said acetate buffer has a pH of between about 4.25 and about 5.25 and a final concentration in said sample of between about 0.05M and about 0.25M.

27. The method of claim 14, wherein said acetate buffer has a pH of between about 4.5 and about 5.0 and a final concentration in said sample of between about 0.05M and about 0.1M.

28. The method of claim 14, wherein said acetate buffer has a pH of about 4.75 and a final concentration in said sample of about 0.1M.

29. The method of claim 14, wherein said acetate buffer comprises sodium acetate.

30. The method of claim 14, wherein said acetate buffer comprises potassium acetate.

31. The method of claim 14, wherein said acetate buffer is essentially free from volume excluding polymers.

32. The method of claim 14, wherein said acetate buffer is essentially free from polyethylene glycol.

33. The method of claim 14, wherein said acetate buffer is sodium acetate with a pH of about 4.75 and a final concentration in said sample of about 0.1M.

34. The method of claim 14, wherein said biological fluid is a murine, bovine or human biological fluid.

35. The method of claim 14, wherein said biological fluid is a cell culture supernatant, whole blood, serum, plasma, ascites fluid, cerebrospinal fluid, bone marrow aspirate, bronco-alveolar washing, urine, semen, vaginal fluid, mucous, saliva, sputum or a clarified lysate from a biological tissue sample.

36. The method of claim 35, wherein said biological fluid is a cleared cell culture supernatant that has already been subjected to low-speed centrifugation.

37. The method of claim 35, wherein said biological fluid is a cell culture supernatant obtained from tumor cells cultured in the presence of serum that contains non-tumor exosomes.

38. The method of claim 35, wherein said biological fluid is a cell culture supernatant obtained from mouse or human tumor cells cultured in the presence of bovine or fetal bovine serum.

39. The method of claim 14, further comprising the step of subjecting said biological fluid to low-speed centrifugation to remove cells, cell debris and large membrane vesicles prior to contact with said acetate buffer.

40. The method of claim 14, wherein the precipitate that contains said tumor-derived extracellular microvesicles after contact with said acetate buffer is collected by low-speed centrifugation.

41. The method of claim 14, further comprising resuspending the collected precipitate containing said tumor-derived extracellular microvesicles in a substantially acetate-free buffer at about neutral pH to provide an isolated population of tumor-derived extracellular microvesicles.

42. The method of claim 14, further comprising identifying or quantifying at least a first biomarker in said tumor-derived extracellular microvesicles.

43. The method of claim 42, wherein said biomarker is an RNA, micro RNA, DNA or protein biomarker.

44. A method of isolating tumor-derived extracellular microvesicles from a biological fluid, comprising precipitating tumor-derived extracellular microvesicles from said biological fluid, wherein said precipitating comprises contacting a sample of said biological fluid with an amount of an acetate buffer effective to precipitate tumor-derived extracellular microvesicles from said biological fluid, and collecting said tumor-derived extracellular microvesicles from the precipitate, thereby isolating said tumor-derived extracellular microvesicles; wherein said acetate buffer has a pH of between about 4.25 and about 5.25 and a final concentration in said sample of between about 0.05M and about 0.25M.

45. A method of isolating tumor-derived extracellular microvesicles from a biological fluid, wherein said tumor-derived extracellular microvesicles have negatively-charged phosphatidylserine on their surface; said method comprising selectively precipitating tumor-derived extracellular microvesicles from said biological fluid, wherein said selectively precipitating comprises contacting a sample of said biological fluid with an acetate buffer at a pH and concentration effective to neutralize the negative surface charge of said phosphatidylserine, thereby selectively precipitating said tumor-derived extracellular microvesicles from said biological fluid; and collecting said tumor-derived extracellular microvesicles from the precipitate, thereby isolating said tumor-derived extracellular microvesicles.

46. A method to obtain tumor-derived extracellular microvesicles from the supernatant of tumor cells cultured in the presence of serum that contains normal extracellular microvesicles, said method comprising selectively precipitating tumor-derived extracellular microvesicles from said supernatant, wherein said selectively precipitating comprises contacting said supernatant with an acetate buffer at a pH and concentration effective to selectively precipitate tumor-derived extracellular microvesicles from said supernatant and collecting the precipitate, thereby obtaining tumor-derived extracellular microvesicles from said supernatant without substantial contamination from normal extracellular microvesicles in said serum.

47. A method to prepare serum that is substantially free from tumor-derived extracellular microvesicles, said method comprising:
  (a) obtaining serum suspected of containing tumor-derived extracellular microvesicles, wherein said tumor-derived extracellular microvesicles are phosphatidylserine-positive extracellular microvesicles that have negatively-charged phosphatidylserine on their surface;
  (b) precipitating tumor-derived extracellular microvesicles from said serum, wherein said precipitating comprises contacting said serum with an acetate buffer at a pH and concentration effective to precipitate tumor-derived extracellular microvesicles from said serum; and
  (c) removing from the serum the precipitate formed in step (b), wherein said precipitate contains said tumor-derived extracellular microvesicles, thereby providing a serum that is substantially free from tumor-derived extracellular microvesicles.

48. A method to detect tumor-derived extracellular microvesicles in a clarified biological fluid, wherein said tumor-derived extracellular microvesicles are phosphatidylserine-positive extracellular microvesicles that have negatively-charged phosphatidylserine on their surface; said method comprising precipitating tumor-derived extracellular microvesicles from said clarified biological fluid, wherein said precipitating comprises contacting said clarified biological fluid with an acetate buffer at a pH and concentration effective to selectively precipitate tumor-derived extracellular microvesicles from said clarified biological fluid; and determining the presence of turbidity in the resultant biological fluid; wherein the presence of turbidity in the resultant biological fluid indicates the detection of tumor-derived extracellular microvesicles.

49. A method to diagnose a patient with cancer, comprising:
(a) detecting tumor-derived extracellular microvesicles in a biological fluid from said patient, wherein said tumor-derived extracellular microvesicles are phosphatidylserine-positive extracellular microvesicles that have negatively-charged phosphatidylserine on their surface, and wherein said detecting comprises:
  (i) precipitating tumor-derived extracellular microvesicles from said biological fluid, wherein said precipitating comprises contacting said biological fluid with an acetate buffer at a pH and concentration effective to selectively precipitate tumor-derived extracellular microvesicles from said biological fluid; and
  (ii) determining the presence of said precipitate in the resultant biological fluid; wherein the presence of said precipitate in the resultant biological fluid indicates the detection of said tumor-derived extracellular microvesicles; and
(b) confirming the presence of cancer by testing for a biomarker or clinical sign of cancer.

50. A method to monitor the tumor-burden of a cancer patient, comprising:
(a) obtaining a series of biological fluid samples from said patient at a plurality of time points;
(b) measuring the amount of tumor-derived extracellular microvesicles in said series of biological fluid samples, wherein said tumor-derived extracellular microvesicles are phosphatidylserine-positive extracellular microvesicles that have negatively-charged phosphatidylserine on their surface, and wherein said measuring comprises:
  (i) selectively precipitating tumor-derived extracellular microvesicles from said series of biological fluid samples, wherein said selectively precipitating comprises contacting said series of biological fluid samples with an acetate buffer at a pH and concentration effective to selectively precipitate tumor-derived extracellular microvesicles from said series of biological fluid samples; and
  (ii) measuring the amount of tumor-derived extracellular microvesicles in the precipitates;
wherein an increase in the amount of tumor-derived extracellular microvesicles is indicative of an increased tumor-burden and a decrease in the amount of said tumor-derived extracellular microvesicles is indicative of a decreased tumor-burden.

* * * * *

UNITED STATES PATENT AND TRADEMARK OFFICE
CERTIFICATE OF CORRECTION

PATENT NO.         : 9,835,626 B2
APPLICATION NO.    : 14/634607
DATED              : December 5, 2017
INVENTOR(S)        : Alan J. Schroit, Philip E. Thorpe and Shelley P. M. Fussey It is certified that error appears in the above-identified patent and that said Letters Patent is hereby corrected as shown below:

In the Claims

Column 46

In Claim 7, Line 23, delete "the" and replace with --said--

In Claim 7, Line 25, insert --said-- before "viral-derived"

In Claim 8, Line 27, insert --said-- before "viral-derived"

Signed and Sealed this
Thirteenth Day of February, 2018

Andrei Iancu
*Director of the United States Patent and Trademark Office*